United States Patent [19]

Antoine et al.

[11] Patent Number: 4,990,515

[45] Date of Patent: Feb. 5, 1991

[54] BENZO[1,8]NAPHTHYRIDINE DERIVATIVES AS ANTIMICROBIALS

[75] Inventors: Michel Antoine, Paris; Michel Barreau, Montgeron; Jean-Francois Desconclois, Paris; Philippe Girard, Arpajon; Guy Picaut, Chevilly Larue, all of France

[73] Assignee: Rhone-Poulenc Sante, France

[21] Appl. No.: 465,316

[22] Filed: Jan. 16, 1990

[30] Foreign Application Priority Data

Jan. 16, 1989 [FR] France .................. 89 00430
Jul. 28, 1989 [FR] France .................. 89 10219

[51] Int. Cl.⁵ .......................................... A01N 43/42
[52] U.S. Cl. ................................ 514/292; 546/14; 546/81
[58] Field of Search .................. 546/258, 110, 14, 81; 71/94; 514/292

[56] References Cited

U.S. PATENT DOCUMENTS

| | | | |
|---|---|---|---|
| 4,133,885 | 1/1979 | Bolhofer et al. | 546/81 |
| 4,169,893 | 10/1979 | Hardtmann | 546/110 |
| 4,229,456 | 10/1980 | Bolhofer et al. | 546/81 |

FOREIGN PATENT DOCUMENTS 132845 2/1985 European Pat. Off. ............. 546/81
3302126 1/1983 Fed. Rep. of Germany ........ 546/81

OTHER PUBLICATIONS

Chem Abstracts, vol. 61, 10666g, (1964).

*Primary Examiner*—Mary C. Lee
*Assistant Examiner*—Robert C. Whittenbaugh
*Attorney, Agent, or Firm*—Morgan & Finnegan

[57] ABSTRACT

New benzo[b][1,8]naphthyridine derivatives of general formula (I), in which R is a hydrogen atom or an alkyl, fluoroalkyl, cycloalkyl (3 to 6 C), alkoxy or alkylamino radical or an amine protective radical and either Hal is a fluorine, chlorine or bromine atom and R' is a hydrogen atom or Hal and R' are simultaneously fluorine atoms, their salts, their preparation and the compositions which contain them.

These new products can be used as antimicrobial agents for topical application or as synthesis intermediates.

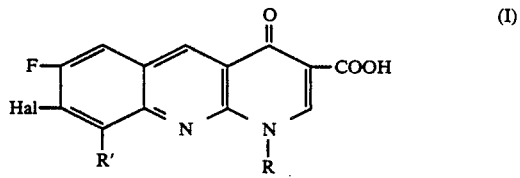

8 Claims, No Drawings

BENZO[1,8]NAPHTHYRIDINE DERIVATIVES AS ANTIMICROBIALS

The present invention relates to new benzo[b][1,8-]naphthyridine derivatives of general formula:

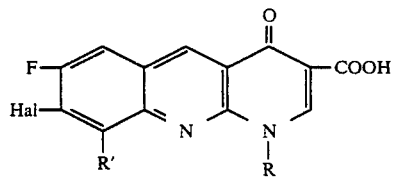

their salts, their preparation and, where appropriate, the compositions which contain them.

Naphthyridine derivatives of structure:

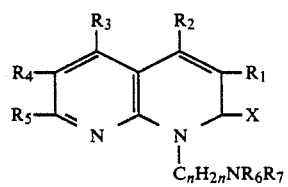

which X can be oxygen and two adjacent radicals of the radicals $R_1$ to $R_5$ can form a benzene ring, have been described in U.S. Pat. Nos. 4,229,456 and 4,133,885.

These products are used as gastric acid secretion inhibitors.

German Patent Application No. 3,302,126 describes hypotensive agents of general formula:

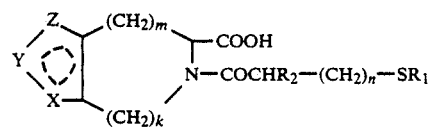

in which the radicals X, Y and Z can be O or a $NR_4$ radical or $CR_5=CR_5$ radical in which the $R_5s$ can form a benzene ring.

In the general formula (I):
the symbol R represents a hydrogen atom, an alkyl or fluoroalkyl radical, a cycloalkyl radical containing 3 to 6 carbon atoms, or an alkoxy or alkylamino radical or represents an amine protective radical, and
either the symbol Hal represents a fluorine, chlorine or bromine atom and the symbol R' represents a hydrogen atom,
or the symbols Hal and R' simultaneously represent fluorine atoms.

It is understood that the alkyl radicals are straight-chain or branched and contain 1 to 4 carbon atoms.

When R represents a protective radical, this radical can be any group which is compatible and the introduction and removal of which does not alter the remainder of the molecule, in particular, the groups described by T. W. GREENE, Protective Groups in Organic Synthesis, A. Wiley-Interscience Publication (1981), or by McOMIE, Protective Groups in Organic Chemistry, Plenum Press (1973).

By way of example, the protective groups can be chosen from the trimethylsilyl, trityl, benzhydryl, tetrahydropyrannyl, formyl, acetyl, chloroacetyl, trichloroacetyl, trifluoroacetyl, methoxycarbonyl, ethoxycarbonyl, t-butoxycarbonyl, trichloroethoxycarbonyl, ethoxymethyl and methoxymethyl radicals.

According to the invention, the benzo[b][1,8]naphthyridine derivative of general formula (I) can be obtained from the corresponding ester of general formula:

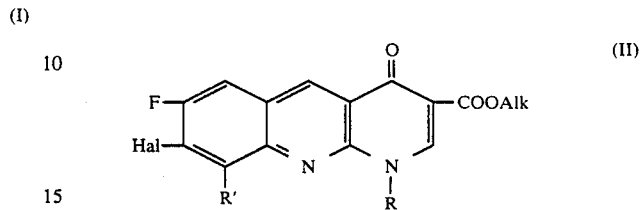

in which R is a hydrogen atom or an alkyl, fluoroalkyl, cycloalkyl, alkoxy, alkylamino or protected alkylamino radical, Hal and R' are defined as above and Alk is a straight-chain or branched alkyl radical, containing 1 to 4 carbon atoms, by any method known for obtaining an acid from an ester without touching the remainder of the molecule, followed, where appropriate, by the introduction of the protective radical R in the 1-position or the removal of the protective group from the alkylamino radical.

When R is a protected alkylamino radical, the protective radical can be any amino protective group compatible with the molecule and the operating conditions of the process. In particular, groups which can be removed simultaneously with the hydrolysis of the ester, for example the formyl radical, are advantageously used.

The preparation of the acid from the ester is generally carried out by acid hydrolysis. The reaction is advantageously carried out in an acetic acid/hydrochloric acid mixture, in sulphuric acid or in methanesulphonic acid, at a temperature of between 60° and 100° C. It is also possible to carry out the reaction by saponification in the presence of potassium hydroxide or sodium hydroxide, in an aqueous-alcoholic medium, at a temperature of between 20° and 80° C.

Where appropriate, the introduction of the protective radical in the 1-position is effected by the methods described in the above references.

The benzo[b][1,8]naphthyridine ester derivative of general formula (II) can be prepared by the action of 3-amino-1,2,4-triazine (to obtain a product for which R is a hydrogen atom), or by the action of a product of general formula:

R—NH₂ (III)

in which R is alkyl, fluoroalkyl, cycloalkyl, alkoxy, alkylamino or protected alkylamino, on a quinoline derivative of general formula:

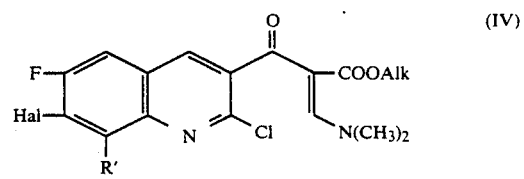

in which R', Hal and Alk are defined as above, followed by cyclization by the action of an acid acceptor.

In general, the reaction of 3-amino-1,2,4-triazine or of the product of general formula (III) is carried out in an organic solvent such as an alcohol (ethanol or methanol for example) or a chlorinated solvent (trichloromethane for example) at a temperature of between 10° and 25° C.

The cyclization is carried out in the presence of 1,8-diazabicyclo[5.4.0]undec-7-ene or of a nitrogenous base, such as, for example, triethylamine, or an excess of the amine employed, in a straight-chain or branched alcohol containing 1 to 4 carbon atoms, at a temperature of between 20° C. and the reflux temperature of the reaction mixture.

The quinoline derivative of general formula (IV) can be obtained from the keto-ester of general formula:

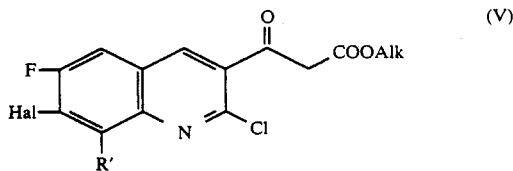
(V)

in which R′, Hal and Alk are defined as above, by the action of a N,N-dimethylformamide acetal of general formula:

(CH$_3$)$_2$N—CH(OAlk$_1$)$_2$ (VI)

in which Alk$_1$ is a straight-chain or branched alkyl radical containing 1 to 4 carbon atoms.

The reaction is generally carried out in an organic solvent such as an ester (ethyl acetate for example) at a temperature of between 60° and 75° C.

The keto-ester of general formula (V) in which R′ is a hydrogen atom and Hal is defined as above can be obtained from 2,7-dichloro-6-fluoroquinoline-3-carboxylic acid or 2-chloro-6,7-difluoroquinoline-3-carboxylic acid as described below in Examples 1 and 6 or from 7-bromo-2-chloro-6-fluoroquinoline-3-carboxylic acid by analogy with this method. In this case, the 3-bromo-4-fluoroaniline used as starting material can be prepared by the method described by W. B. Austin et al., J. Org. Chem., 46 (11), 2280 (1981).

The keto-ester of general formula (V) in which R′ and Hal are simultaneously fluorine atoms can be obtained from 2-chloro-6,7,8-trifluoroquinoline-3-carboxylic acid as described below in Example 9.

The new products according to the invention can be used as intermediates for the preparation of benzo[b][1,8]naphthyridine derivatives of general formula:

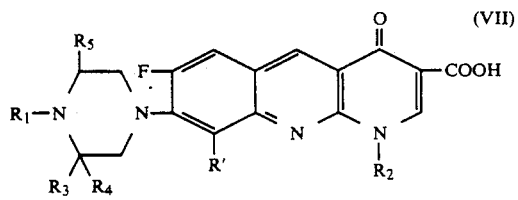
(VII)

in which:

R$_1$ represents a hydrogen atom or an alkyl or hydroxyalkyl radical,

R$_2$ represents a hydrogen atom or an alkyl or fluoroalkyl radical, a cycloalkyl radical containing 3 to 6 carbon atoms or an alkoxy or alkylamino radical, R$_3$ represents a hydrogen atom or an alkyl radical, and R$_4$ and R$_5$ are different and represent a hydrogen atom or an alkyl radical, or R$_3$ is a hydrogen atom or an alkyl or cycloalkyl radical and R$_4$ and R$_5$ are hydrogen atoms, and R′ represents a hydrogen or fluorine atom, and their salts, their hydrates and, where appropriate, their isomers.

The products of general formula (VII) can be obtained by substitution of a piperazine of general formula:

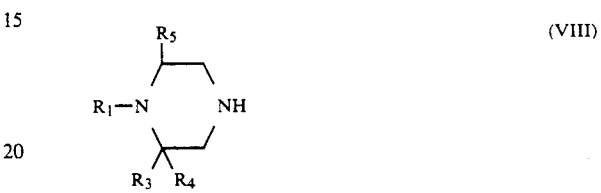
(VIII)

in which R$_1$, R$_3$, R$_4$ and R$_5$ are as defined above, on a benzo[b]1,8]naphthyridine of general formula (I), followed, if appropriate, if R$_1$ is a hydrogen atom and if it is desired to obtain a benzo[b][1,8]naphthyridine derivative in which R is methyl, by the conversion of the product obtained to a 8-(4-methyl-1-piperazinyl)benzo[b][1,8]naphthyridine and followed, if appropriate, by the removal of the protective radical in the 1-position.

The action of the piperazine derivative of general formula (VIII) generally takes place in the presence of an excess of this derivative as an acid acceptor or in the presence of an organic or inorganic acid acceptor in suitable organic solvents. It is possible to carry out the reaction with or without solvents, at a temperature between 30° and 120° C. When it is carried out in the presence of a solvent, the reaction advantageously takes place in solvents such as pyridine, dimethylformamide, dimethyl sulphoxide or acetonitrile.

It is understood that in the case where it is desired to obtain a product in which the symbol R$_2$ is a hydrogen atom it is preferable to carry out the reaction starting from a benzonaphthyridine derivative in which R is a protective radical. The protection, and the removal of the protective radical after the reaction, are carried out by customary methods.

Where appropriate, the subsequent operation for the methylation of the piperazinyl radical is advantageously carried out by the action of formol in the presence of formic acid. The reaction is generally carried out in an aqueous medium, at a temperature of between 90° and 100° C.

The new products according to the present invention and the products of general formula (VII) can, if necessary, be purified by physical methods such as crystallization or chromatography.

The products according to the present invention and the products of general formula (VII) can be converted to metal salts or addition salts with nitrogenous bases by the methods known per se. These salts can be obtained by the action of a metal (for example alkali metal or alkaline earth metal)-containing base, ammonia or an amine on a product according to the invention in an appropriate solvent, such as an alcohol, an ether or water, or by an exchange reaction with a salt of an organic acid. The salt formed precipitates, after concentration of its solution if necessary; it is separated off by filtration, decanting or lyophilization.

The new benzo[b][1,8]naphthyridine derivatives of general formula (VII) and their pharmaceutically acceptable salts have antibacterial properties. They display a remarkable in vitro and in vivo activity on Gram-positive germs and, in a general manner, on the germs responsible for the majority of the infections of the upper and lower air passages.

In vitro, the products of general formula (VII) have been shown to be active at a concentration of between 0.12 and 50 μg/cm$^3$ on *Staphylococcus aureus* IP 8203.

In vivo, the products of general formula (VII) have been shown to be active against experimental infections of mice with *Staphylococcus aureus* IP 8203 at doses of between 2 and 150 mg/kg administered orally or subcutaneously.

Moreover, these products are of low toxicity. Their LD$_{50}$ is generally greater than 500 mg/kg when administered subcutaneously to mice.

The new benzo[b]naphthyridine derivatives of general formula (I) in which R is other than a protective radical, and their salts, are also of particular value because of their inherent in vitro antibacterial properties and, due to this fact, can be used in particular for local application in the case of cutaneous infections with staphylococci.

The benzo[b][1,8]naphthyridine derivatives according to the invention have, in fact, been shown to be active in vitro at concentrations of between 0.2 and 500 μg/cm$^3$ on *Staphylococcus aureus* IP 8203.

Their LD$_{50}$ is likewise greater than 500 mg/kg when administered subcutaneously to mice.

The following may be mentioned as examples of pharmaceutically acceptable salts: the salts with the alkali metals (sodium, potassium, lithium) or with the alkaline earth metals (magnesium, calcium), the ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, dibenzylamine) and the addition salts with inorganic acids (hydrochlorides, hydrobromides, sulphates, nitrates, phosphates) or organic acids (succinates, fumarates, maleates, p-toluenesulphonates).

The products of general formula (I) of particular interest are those in which R represents a hydrogen atom, an alkyl radical containing 1 to 4 carbon atoms or a fluoroethyl, cyclopropyl, methoxy or methylamino radical, and either Hal represents a fluorine or chlorine atom and R' represents a hydrogen atom, or Hal and R' simultaneously represent fluorine atoms.

And amongst these products, the following products are very particularly interesting:

7,8-difluoro-1-methyl-4-oxo-1,4-dihydro-benzo[b][1,8-]naphthyridine-3-carboxylic acid;
8-chloro-7-fluoro-1-methyl-4-oxo-1,4-dihydro-benzo[b][1,8]naphthyridine-3-carboxylic acid;
1-methyl-4-oxo-7,8,9-trifluoro-1,4-dihydro-benzo[b][1,8]naphthyridine-3-carboxylic acid;
7,8-difluoro-1-methoxy-4-oxo-1,4-dihydro-benzo[b][1,8]naphthyridine-3-carboxylic acid;
1-cyclopropyl-7,8-difluoro-4-oxo-1,4-dihydro-benzo[b][8]naphthyridine-3-carboxylic acid.

The following examples, given as non-limiting examples, illustrate the present invention.

EXAMPLE 1

A suspension of 15 g of 8-chloro-3-ethoxycarbonyl-7-fluoro-1-methyl-4-oxo-1,4-dihydro-benzo[b][1,8]naphthyridine in 150 cm$^3$ of acetic acid and 50 cm$^3$ of hydrochloric acid as a 17.5% aqueous solution is heated at a temperature close to 100° C., with stirring, for 4 hours. After cooling to a temperature close to 20° C., the product is drained and washed with twice 150 cm$^3$ of ethanol and then twice 100 cm$^3$ of diethyl ether. 12.7 g of 8-chloro-7-fluoro-1-methyl-4-oxo-1,4-dihydro-benzo[b][1,8]naphthyridine-3-carboxylic acid are obtained in the form of a beige solid which sublimes at 400°–405° C.

The 8-chloro-3-ethoxycarbonyl-7-fluoro-1-methyl-4-oxo-1,4-dihydro-benzo[b][1,8]naphthyridine is prepared in the following manner:

Methylamine is bubbled into a stirred suspension of 19.3 g of ethyl 2-(2,7-dichloro-6-fluoro-quinoline-3-carbonyl)-3-dimethylaminoacrylate in 250 cm$^3$ of ethanol, kept at between 10° and 15° C., until 16 g of gas have been absorbed. The temperature is allowed to rise to about 20° C., 0.8 g of 1,8-diazabicyclo[5.4.0]undec-7-ene (DBU) is added and the mixture is heated at a temperature close to 75° C. for 2 hours. After cooling to about 20° C., the product is drained and washed with twice 150 cm$^3$ of ethanol and twice with 100 cm$^3$ of diethyl ether. 15 g of 8-chloro-3-ethoxycarbonyl-7-fluoro-1-methyl-4-oxo-1,4-dihydro-benzo[b][1,8]naphthyridine are obtained in the form of a yellow solid melting at 360°–362° C., which is used for the subsequent steps without further purification.

The ethyl 2-(2,7-dichloro-6-fluoro-quinoline-3-carbonyl)-3-dimethylaminoacrylate is prepared in the following manner:

A suspension of 16.5 g of ethyl 3-(2,7-dichloro-6-fluoro-3-quinolyl)-3-oxopropionate in 160 cm$^3$ of ethyl acetate and 19 cm$^3$ of N,N-dimethylformamide dimethyl acetal is heated at a temperature close to 75° C., with stirring, for 2 hours. The reaction mixture is concentrated to dryness under reduced pressure (20 kPa) at 50° C. The dry extract is taken up in 50 cm$^3$ of diisopropyl ether, drained and washed with twice 10 cm$^3$ of diisopropyl ether. 16.57 g of ethyl 2-(2,7-dichloro-6-fluoro-quinoline-3-carbonyl)-3-dimethylaminoacrylate are obtained in the form of an orange solid melting at 122° C. This product is used for the subsequent steps without further purification.

The ethyl 3-(2,7-dichloro-6-fluoro-3-quinolyl)-3oxopropionate is prepared in the following manner:

A suspension of 38.75 g of 2,7-dichloro-6-fluoroquinoline-3-carboxylic acid in 410 cm$^3$ of trichloromethane and 24 cm$^3$ of thionyl chloride is heated at a temperature close to 60° C., with stirring, for 6 hours. The solution obtained is concentrated to dryness under reduced pressure (20 kPa) at 50° C. The dry extract is twice taken up in a total of 200 cm$^3$ of toluene and again concentrated under reduced pressure under the same conditions as above. The yellow solid obtained, which melts at 124° C., is dissolved in 230 cm$^3$ of anhydrous tetrahydrofuran. The solution obtained is introduced dropwise, with stirring, in the course of 30 minutes, at between 5° and 10° C., into 200 cm$^3$ of a solution of magnesium chelate in tetrahydrofuran, the preparation of which is described below. The temperature is allowed to rise to 20° C. and the mixture is stirred for 1 hour and a half at this temperature. The solution obtained is introduced dropwise, with vigorous stirring, at a temperature close to 5° C., into 1 liter of 0.5 N sulphuric acid. The temperature of the suspension obtained is allowed to rise to 20° C. and the suspension is stirred for a further 2 hours at this temperature. The suspension is extracted with 1 liter of ethyl acetate and the organic and aqueous phases are filtered through diatomaceous silica for filtration, which enables a small amount of insoluble matter to be removed, and the aqueous phase is extracted twice more with 500 cm³ of ethyl acetate. The combined organic extracts are washed with twice 500 cm³ of water, dried over magnesium sulphate and filtered and the filtrate is concentrated to dryness under reduced pressure (20 kPa) at 40° C. The residue is taken up in 100 cm³ of diisopropyl ether at 20° C., drained and washed with twice 30 cm³ of diisopropyl ether. 40.55 g of ethyl 3-(2,7-dichloro-6-fluoro-3-quinolyl)-3-oxopropionate are obtained in the form of a beige solid melting at 112°-114° C. This product is used for the subsequent steps without further purification.

Preparation of the magnesium chelate of ethyl monomalonate:

5 cm³ of absolute ethanol, 0.2 cm³ of tetrachloromethane and 2 g of ethyl monomalonate ar added progressively to 6.9 g of magnesium turnings. After heating, a solution of 23.8 g of ethyl monomalonate in 450 cm³ of ethanol is added in the course of 15 minutes. The mixture is heated at a temperature close to 78° C. for 20 hours and concentrated under reduced pressure (20 kPa) at 50° C. The residue is taken up in twice 100 cm³ of toluene and concentrated under reduced pressure under the same conditions as above. The grey powder obtained is brought into solution by adding anhydrous tetrahydrofuran so as to obtain a total volume of 200 cm³.

The ethyl monomalonate was prepared by the method described by D. S. Breslow, E. Baumgarten, C. R. Hauser, J. Am. Chem. Soc., 66, 1287 (1944) and distilled under reduced pressure (boiling point=132° C./2.7 kPa).

The 2,7-dichloro-6-fluoroquinoline-3-carboxylic acid is prepared in the following manner:

A solution of 89.3 g of potassium permanganate in 1.4 liters of water is added in the course of 1 hour and while keeping the temperature between 10° and 14° C. to a stirred suspension, cooled to 10° C., of 69.5 g of 2,7-dichloro-6-fluoro-3-formyl-1,4-dihydroquinoline in 282 cm³ of 2 N aqueous potassium hydroxide solution and 282 cm³ of water. The temperature is allowed to rise to about 20° C. and the mixture is stirred for a further 30 minutes at this temperature. 26 g of sodium dithionite are added, the mixture is stirred for 10 minutes at a temperature close to 20° C. and filtered through diatomaceous silica for filtration and the filter cake is washed with twice 250 cm³ of water. The filtrate and the aqueous washing phases are combined and 90 cm³ of a 35% aqueous solution of hydrochloric acid are added. The precipitate formed is extracted with 4 times 500 cm³ of ethyl acetate. The combined organic extracts are washed with 3 times 500 cm³ of water, dried over magnesium sulphate, filtered and the filtrate is concentrated under reduced pressure (20 kPa) at 50° C. The residue is taken up in 350 cm³ of diethyl ether, drained and washed with twice 200 cm³ of diethyl ether. 45 g of 2,7-dichloro-6-fluoroquinoline-3-carboxylic acid are obtained in the form of a beige solid melting at 230° C. which is used for the subsequent steps without further purification.

The 2,7-dichloro-6-fluoro-3-formyl-1,4-dihydroquinoline was prepared in the following manner:

55.6 cm³ of phosphoryl chloride are added in the course of 30 minutes, with stirring, at between 10° and 15° C., to a mixture of 250 cm³ of trichloromethane and 54 cm³ of dimethylformamide and the mixture is stirred for 1 hour at a temperature close to 20° C. 52 g of 7-chloro-6-fluoro-3,4-dihydrocarbostyril are added progressively, with vigorous stirring, in the course of 10 minutes, at about 20° C. to the solution obtained. The suspension obtained is heated to a temperature close to 60° C. and is kept at this temperature for a further 2 hours, with stirring. The reaction mixture is concentrated under reduced pressure (20 kPa) at 50° C. until a pasty mixture is obtained. A mixture of 250 cm³ of water and 250 g of crushed ice is added, with vigorous stirring. The solid obtained is drained at about 5° C. and washed with 4 times 125 cm³ of water at 5° C. The moist product obtained and 58 g of sodium acetate are added simultaneously, in the course of 1 hour, to 500 cm³ of water at 90° C. in such a way as to maintain the pH at about 6. The mixture is stirred for a further 15 minutes at 90° C., the temperature is allowed to fall to about 50° C. and the product is drained at this temperature and washed with 3 times 250 cm³ of water at about 20° C. 54.3 g of 2,7-dichloro-6-fluoro-3-formyl-1,4-dihydroquinoline are obtained in the form of a yellow solid melting at 260° C. which is used in this form for the subsequent steps.

The 7-chloro-6-fluoro-3,4-dihydrocarbostyril is prepared in the following manner:

350 g of aluminium chloride are added in the course of 5 minutes, with vigorous stirring, to 174.4 g of 3'-chloro-4'-fluoro-3-(N-chloro)-propionanilide. The solid mixture is heated to about 60° C. in the course of 30 minutes. The temperature rises on its own to about 80° C. and the reaction mixture becomes liquid. It is then heated to 110° C. in the course of 15 minutes and kept at between 110° and 120° C. for 3 hours. The reaction mixture (at about 110° C.) is poured, in the course of 10 minutes, with vigorous stirring, into a mixture of 550 cm³ of 35% hydrochloric acid and 500 g of crushed ice. The temperature is allowed to rise to 20° C. and the product is drained and washed with 6 times 500 cm³ of water.

The moist product is recrystallized from 1.2 liters of ethanol. 108 g of 7-chloro-6-fluoro-3,4-dihydrocarbostyril are obtained in the form of a beige solid melting at 215° C.

The 3'-chloro-4'-fluoro-3-(N-chloro)-propionanilide was prepared in the following manner:

A solution of 127 g of 3-chloropropionyl chloride in 200 cm³ of acetone is added, with stirring, in the course of 35 minutes, to a solution, at a temperature close to 55° C., of 291 g of 3-chloro-4-fluoroaniline in 500 cm³ of acetone and the mixture is kept at this temperature for 2 hours. After cooling to about 20° C., the insoluble matter is removed by filtration and washed with twice 200 cm³ of acetone. The filtrate and the combined washings are poured into 2 liters of water and 1 kg of ice, with stirring. The temperature is allowed to rise to about 20° C. and the mixture is extracted with 4 times 500 cm³ of dichloromethane. The combined organic extracts are washed with 3 times 500 cm³ of water, dried over magnesium sulphate, stirred for 15 minutes with 6 g of Norit vegetable charcoal, filtered through diatomaceous silica for filtration and concentrated under reduced pressure (20 kPa) at 50° C. The solid obtained is recrystallized from a mixture of 133 cm³ of cyclohexane and 67 cm³ of diisopropyl ether. 176 g of 3'-chloro-4'-fluoro-3-(N-chloro)-propionanilide are obtained in the form of a beige solid melting at 94° C., which is used in this form for the subsequent steps.

EXAMPLE 2

Carrying out the reaction under the conditions described in Example 1 but starting from 10.5 g of 8-chloro-7-fluoro-3-ethoxycarbonyl-1-ethyl-4-oxo-1,4-dihydro-benzo[b][1,8]naphthyridine. 9.3 g of 8-chloro-1-ethyl-7-fluoro-4-oxo-1,4-dihydro-benzo[b][1,8]naphthyridine-3-carboxylic acid are obtained in the form of a beige solid melting at 380° C.

The 8-chloro-3-ethoxycarbonyl-1-ethyl-7-fluoro-4-oxo-1,4-dihydro-benzo[b][1,8]naphthyridine is prepared in the following manner:

16 g of ethylamine are added, in the course of 5 minutes, at between 10° and 15° C., to a stirred suspension of 13.5 g of ethyl 2-(2,7-dichloro-6-fluoroquinoline-3-carbonyl)-3-dimethylaminoacrylate in 135 cm³ of ethanol, the temperature is allowed to rise to about 20° C., 0.5 g of DBU is added and the mixture is heated, with stirring, for 2 hours at a temperature close to 75° C. After cooling to a temperature close to 20° C., the precipitate is drained and washed with twice 100 cm³ of ethanol and twice 100 cm³ of diethyl ether. 10.4 g of 8-chloro-3-ethoxycarbonyl-1-ethyl-7-fluoro-4-oxo-1,4-dihydro-benzo[b][1,8]naphthyridine are obtained in the form of a yellow solid melting at 300°–301° C., which is used for the subsequent steps without further purification.

EXAMPLE 3

A suspension of 16.4 g of 8-chloro-3-ethoxycarbonyl-7-fluoro-1-(N-formyl-N-methylamino)-4-oxo-1,4-dihydro-benzo[b][1,8]naphthyridine in 164 cm³ of acetic acid and 164 cm³ of an aqueous 17.5% hydrochloric acid solution is heated at a temperature close to 100° C., with stirring, for 4 hours. After cooling to a temperature close to 10° C., 165 cm³ of 30% slaked lime is added at between 10° and 20° C. The product is drained and washed with 3 times 150 cm³ of water, 3 times 150 cm³ of ethanol and 3 times 150 cm³ of diethyl ether. 13.64 g of 8-chloro-7-fluoro-1-methylamino-4-oxo-1,4-dihydro-benzo[b][1,8]naphthyridine-3-carboxylic acid are obtained in the form of a yellow solid melting at 354°–356° C.

The 8-chloro-3-ethoxycarbonyl-7-fluoro-1-(N-formyl-N-methylamino)-4-oxo-1,4-dihydro-benzo[b][1,8]naphthyridine is prepared under the conditions of Example 1 but starting from 19.25 g of ethyl 2-(2,7-dichloro-6-fluoroquinoline-3-carbonyl)-3-dimethylaminoacrylate, 4.05 g of N-formyl-N-methylhydrazine and 1.6 g of DBU in 200 cm³ of ethanol. 16.4 g of 8-chloro-3-ethoxycarbonyl-7-fluoro-1-(N-formyl-N-methylamino)-4-oxo-1,4-dihydro-benzo[b][1,8]naphthyridine are obtained in the form of a colourless solid melting at 296°–298° C., which can be used for the subsequent steps without further purification.

The N-formyl-N-methylhydrazine can be prepared by the method described by Carl Th. Pedersen, Acta Chem. Scand., 18(9), 2199 (1964).

EXAMPLE 4

Carrying out the reaction under the conditions of Example 1 but starting from 6.1 g of 8-chloro-1-cyclopropyl-3-ethoxycarbonyl-7-fluoro-4-oxo-1,4-dihydro-benzo[b][1,8]naphthyridine, 4.85 g of 8-chloro-1-cyclopropyl-7-fl obtained in the form of a yellow solid melting at 330° C.

The 8-chloro-1-cyclopropyl-3-ethoxycarbonyl-7-fluoro-4-oxo-1,4-dihydro-benzo[b][1,8]naphthyridine is prepared under the following conditions:

A solution of 20.6 g of ethyl 2-(2,7-dichloro-6-fluoroquinoline-3-carbonyl)-3-dimethylaminoacrylate and 6 g of cyclopropylamine in 100 cm³ of trichloromethane is stirred at a temperature close to 20° C. for 24 hours. The reaction mixture is concentrated under reduced pressure (20 kPa) at 50° C. The residue is taken up in 180 cm³ of ethanol and 10 g of DBU and the solution obtained is heated at a temperature close to 78° C. for 4 hours. After cooling to a temperature close to 20° C., the precipitate obtained is drained and washed with twice 60 cm³ of ethanol. 13.65 g of 8-chloro-1-cyclopropyl-3-ethoxycarbonyl-7-fluoro-4-oxo-1,4-dihydro-benzo[b][1,8]naphthyridine are obtained in the form of a pale yellow solid melting at 256° C., which is used for the subsequent steps without further purification.

EXAMPLE 5

A suspension of 1.88 g of 8-chloro-3-ethoxycarbonyl-7-fluoro-4-oxo-1-tert.-butyl-1,4-dihydro-benzo[b][1,8-]naphthyridine in 10 cm³ of ethanol, 5 cm³ of water and 15 cm³ of 2 N aqueous potassium hydroxide solution is heated at a temperature close to 75° C., with stirring, for one hour. 2 cm³ of acetic acid are added to the solution obtained. The precipitate formed is drained and washed with 3 times 10 cm³ of water and 3 times 10 cm³ of ethanol. After recrystallizing once from 50 cm³ of dimethylformamide, 1.7 g of 8-chloro-7-fluoro-4-oxo-1-tert.-butyl-1,4-dihydro-benzo[b][1,8]naphthyridine-3-carboxylic acid are obtained in the form of a yellow solid melting at 398° C.

The 8-chloro-3-ethoxycarbonyl-7-fluoro-4-oxo-1-tert.-butyl-1,4-dihydro-benzo[b][1,8]naphthyridine is prepared under the conditions of Example 4 but starting from 8.86 g of ethyl 2-(2,7-dichloro-6-fluoroquinoline-3-carbonyl)-3-dimethylaminoacrylate and 4.03 g of tert.-butylamine in 45 cm³ of trichloromethane and then in 4.53 g of DBU and 45 cm³ of ethanol. 5 g of 8-chloro-3-ethoxycarbonyl-7-fluoro-4-oxo-1-tert.-butyl-1,4-dihydro-benzo[b][1,8]naphthyridine are obtained in the form of a yellow solid melting at 239° C.

EXAMPLE 6

A suspension of 1.95 g of 1-cyclopropyl-3-ethoxycarbonyl-7,8-difluoro-4-oxo-1,4-dihydro-benzo[b][1,8-]naphthyridine in 20 cm³ of 17.5% hydrochloric acid and 20 cm³ of acetic acid is heated at a temperature close to 100° C. for 1 hour 30 minutes. After cooling to about 20° C., the reaction mixture is poured into 100 cm³ of water. Tho precipitate is drained and washed with 3 times 20 cm³ of water. After recrystallizing once from a mixture of 30 cm³ of dimethylformamide and 30 cm³ of ethanol, 1.31 g of 1-cyclopropyl-7,8-difluoro-4-oxo-1,4-dihydro-benzo[b][1,8]naphthyridine-3-carboxylic acid are obtained in the form of a yellow solid melting at 284°–285° C.

The 1-cyclopropyl-3-ethoxycarbonyl-7,8-difluoro-4-oxo-1,4-dihydro-benzo[b][1,8]naphthyridine is prepared in the following manner:

A stirred suspension of 5.27 g of ethyl 2-(2-chloro-6,7-difluoroquinoline-3-carbonyl)-3-cyclopropylaminoacrylate in 2.22 g of 1,8-diazabicyclo[5.4.0]undec-7-ene (DBU) and 120 cm³ of ethanol is heated at a temperature close to 75° C. for 35 minutes. After cooling to about 20° C., the reaction mixture is taken up in 100 cm³ of water and extracted once with 100 cm³ and twice with 50 cm³ of trichloromethane. The combined organic extracts are washed with 3 times 50 cm³ of water, dried over magnesium sulphate, filtered and concentrated under reduced pressure (20 kPa) at a temperature close to 20° C. The dry extract obtained is taken up in 30 cm³ of diisopropyl ether, drained and recrystallized from a mixture of 75 cm³ of ethanol and 75 cm³ of dimethylformamide. 3.57 g of 1-cyclopropyl-3-ethoxycarbonyl-7,8-difluoro-4-oxo-1,4-dihydro-benzo[b][1,8]naphthyridine are obtained in the form of a yellow solid melting at 229°-230° C.

The ethyl 2-(2-chloro-6,7-difluoroquinoline-3-carbonyl)-3-cyclopropylaminoacrylate is prepared in the following manner:

A solution of 6.25 g of ethyl 2-(2-chloro-6,7-difluoroquinoline-3-carbonyl)-3-dimethylaminoacrylate in 2.91 g of cyclopropylamine and 25 cm³ of trichloromethane is stirred for 3 hours at a temperature close to 20° C. The reaction mixture is concentrated under reduced pressure (20 kPa) at a temperature close to 50° C. The dry extract is taken up in 50 cm³ of diisopropyl ether, drained and then washed with 20 cm³ of the same solvent.

5.27 g of ethyl 2-(2-chloro-6,7-difluoroquinoline-3-carbonyl)-3-cyclopropylaminoacrylate are obtained in the form of an orange solid melting at 116°-117° C. This product is used for the subsequent steps without further purification.

The ethyl 2-(2-chloro-6,7-difluoroquinoline-3-carbonyl)-3-dimethylaminoacrylate is prepared in the following manner:

A suspension of 6.17 g of ethyl 3-(2-chloro-6,7-difluoro-3-quinolyl)-3-oxopropionate in 7.15 g of N,N-dimethylformamide dimethyl acetal and 60 cm³ of ethyl acetate is heated at a temperature close to 75° C. for 1 hour 15 minutes. The reaction mixture is concentrated to dryness under reduced pressure (20 kPa) at about 50° C. The residue is taken up in 50 cm³ of diisopropyl ether, drained and washed with 3 times 25 cm³ of the same solvent. 6.65 g of ethyl 2-(2-chloro-6,7-difluoroquinoline-3-carbonyl)-3-dimethylaminoacrylate are obtained in the form of an orange solid melting at 140° C.

The ethyl 3-(2-chloro-6,7-difluoro-3-quinolyl)-3-oxopropionate is prepared in the following manner:

A suspension of 14.13 g of 2-chloro-6,7-difluoroquinoline-3-carboxylic acid in 29 cm³ of thionyl chloride and 220 cm³ of trichloromethane is heated at a temperature close to 60° C. for 4 hours. The solution obtained is concentrated to dryness under reduced pressure (20 kPa) at about 60° C. The residue obtained is taken up in 75 cm³ of n-hexane, drained and washed with twice 60 cm³ of the same solvent. The 14.4 g of yellow solid obtained are poured into solution in 115 cm³ of tetrahydrofuran. This solution is introduced dropwise, with stirring, in the course of 35 minutes, at between 5° and 10° C., into 70 cm³ of a solution of magnesium chelate of ethyl monomalonate in tetrahydrofuran, prepared under the conditions described below. The temperature is allowed to rise to about 20° C. and the mixture is stirred for a further 2 hours under these conditions. The solution obtained is introduced dropwise, with stirring, in the course of 30 minutes, at a temperature close to 5° C., into 560 cm³ of 0.5N sulphuric acid. The temperature of the suspension obtained is allowed to rise to 20° C. and the suspension is then stirred for a further 1 hour and a half at this temperature. It is extracted with 3 times 250 cm³ of ethyl acetate. The combined organic extracts are washed with twice 250 cm³ of water, dried over magnesium sulphate, filtered and concentrated to dryness under reduced pressure (20 kPa) at 50° C. The residue obtained is taken up in 50 cm³ of n-hexane containing 20% of diisopropyl ether, drained, washed with 10 cm³ of the same mixture and recrystallized from 60 cm³ of isopropanol containing 30% of n-hexane. 11.84 g of ethyl 3-(2-chloro-6,7-difluoro-3-quinolyl)-3-oxopropionate are obtained in the form of a cream solid melting at 107° C.

Preparation of the magnesium chelate of ethyl monomalonate:

2 cm³ of absolute ethanol, 0.1 cm³ of tetrachloromethane and 1 g of ethyl monomalonate are added progressively to 2.78 g of magnesium turnings. After heating, a solution of 9 g of ethyl monomalonate in 180 cm³ of ethanol is added in the course of 15 minutes. The mixture is heated for 20 hours at a temperature close to 75° C. and concentrated under reduced pressure (20 kPa) at 50° C. The residue is taken up in twice 100 cm³ of toluene and the mixture is concentrated under reduced pressure under the same conditions as above. The grey powder obtained is brought into solution by adding anhydrous tetrahydrofuran so as to obtain a total volume of 70 cm³.

The 2-chloro-6,7-difluoroquinoline-3-carboxylic acid was prepared in the following manner:

A solution of 115 g of potassium permanganate in 1.215 liters of water is added in the course of 1 hour, while keeping the temperature between 10° and 14° C., to a stirred suspension, cooled to 10° C., of 70.18 g of 2-chloro-6,7-difluoro-3-formyl-1,4-dihydroquinoline in 970 cm³ of N aqueous potassium hydroxide solution. The temperature is allowed to rise to about 20° C. and the mixture is stirred for a further 30 minutes at this temperature. 38.5 g of sodium dithionite are added, the mixture is stirred for 10 minutes at a temperature close to 20° C. and filtered through diatomaceous silica and the filter cake is washed with 3 times 200 cm³ of water. The filtrate and the aqueous washing phases are combined and 140 cm³ of 35% aqueous hydrochloric acid solution are added. The precipitate formed is extracted with 4 times 800 cm³ of ethyl acetate. The combined organic extracts are washed with twice 500 cm³ of water, dried over magnesium sulphate, filtered and concentrated under reduced pressure (20 kPa) at 50° C. The residue is taken up in 400 cm³ of diethyl ether, drained and washed with twice 200 cm³ of the same solvent. 49.2 g of 2-chloro-6,7-difluoroquinoline-3-carboxylic acid are obtained in the form of a beige solid melting at 232° C., which is used for the subsequent steps without further purification.

The 2-chloro-6,7-difluoro-3-formyl-1,4-dihydroquinoline was prepared in the following manner:

76.9 cm³ of phosphoryl chloride are added in the course of 30 minutes, with stirring, at between 10° and 15° C., to a mixture of 800 cm³ of trichloromethane and 74.35 cm³ of dimethylformamide and the mixture is stirred for 1 hour at a temperature close to 20° C. 65.8 g of 6,7-difluoro-3,4-dihydrocarbostyril are added in the course of 10 minutes, at about 20° C., with vigorous stirring, to the solution obtained The solution obtained is heated to a temperature close to 60° C. and kept at this temperature for 2 hours. The reaction mixture is concentrated under reduced pressure (20 kPa) at 50° C. until a pasty mixture is obtained. A mixture of 500 g of ice and 500 cm³ of water is added, with vigorous stirring. The solid obtained is drained at about 5° C. and washed with 3 times 300 cm³ of water at 5° C. The moist product obtained and 60 g of sodium acetate are added simultaneously, in the course of 1 hour, to 1.5 liters of water at 90° C., in such a way as to maintain the pH at about 6. The mixture is stirred for a further 30 minutes at 90° C., the temperature is allowed to fall to about 50° C. and the product is drained at this temperature and washed with 3 times 300 cm³ of water at about 20° C. 70.18 g of 2-chloro-6,7-difluoro-3-formyl-1,4-dihydroquinoline are obtained in the form of a yellow solid melting at 260° C., which is used in this form for the subsequent steps.

The 6,7-difluoro-3,4-dihydrocarbostyril is obtained in the following manner:

134 g of aluminium chloride are added to 67 g of 3',4'-difluoro-3-(N-chloro)-propionanilide with vigorous stirring and then, after about 2 minutes, a further 135.9 g of 3',4'-difluoro-3-(N-chloro)-propionanilide and 272 g of aluminium chloride are added in small fractions in the course of 15 minutes. The temperature rises on its own to about 60° C. and the reaction mixture becomes liquid. It is then heated to 110° C. in the course of 20 minutes and kept at between 110° and 120° C. for 2 hours. The reaction mixture.(at about 110° C.) is poured in the course of 10 minutes, with vigorous stirring, into a mixture of 840 cm³ of 35% hydrochloric acid and 1 kg of crushed ice. The temperature is allowed to rise to about 20° C. and the product is drained and washed with 600 cm³ of water, twice 300 cm³ of ethanol at 5° C. and twice 400 cm³ of diethyl ether at about 20° C. 131.58 g of 6,7-difluoro-3,4-dihydrocarbostyril are obtained in the form of a beige solid melting at 216° C., which is used in this form for the subsequent steps.

The 3',4'-difluoro-3-(N-chloro)-propionanilide is prepared in the following manner:

139.16 g of 3-chloro-propionyl chloride are added, with stirring, in the course of 1 hour and a half to a solution of 125 g of 3,4-difluoroaniline in 80 cm³ of pyridine and 1.5 liters of acetone heated to a temperature close to 55° C. and the mixture is kept at this temperature for 1 hour and a half. After cooling to about 20° C., the solution is poured, with stirring, into a mixture of 1 liter of water and 500 g of crushed ice The temperature is allowed to rise to about 20° C. and the mixture is extracted with 3 times 500 cm³ of dichloromethane. The combined organic extracts are washed with 500 cm³ of N hydrochloric acid and 5 times 500 cm³ of water, dried over magnesium sulphate, filtered and concentrated under reduced pressure (20 kPa) at about 50° C. The solid obtained is taken up in 500 cm³ of n-hexane, drained and washed with twice 100 cm³ of the same solvent 202.9 g of 3',4'-difluoro-3-(N-chloro)-propionanilide are obtained in the form of a beige solid melting at 76° C., which is used for the subsequent steps without further purification.

EXAMPLE 7

A suspension of 2.78 g of 3-ethoxycarbonyl-7,8-difluoro-1-methoxy-4-oxo-1,4-dihydro-benzo[[b][1,8-]naphthyridine in 30 cm³ of 17.5% of hydrochloric acid and 30 cm³ of acetic acid is heated at a temperature close to 100° C. for 1 hour. After cooling to about 20° C., the reaction mixture is poured into 100 cm³ of water. The precipitate formed is drained and washed with 3 times 30 cm³ of water and twice 5 cm³ of ethanol. After recrystallizing from 100 cm³ of dimethylformamide containing 20% of ethanol, 2.03 g of 7,8-difluoro-1-methoxy-4-oxo-1,4-dihydro-benzo[b][18]naphthyridine-3-carboxylic acid are obtained in the form of a yellow solid melting at 325°-327° C.

The 3-ethoxycarbonyl-7,8-difluoro-1-methoxy-4-oxo-1,4-dihydro-benzo[b][1,8]naphthyridine is prepared under the following conditions:

2.13 g of triethylamine are added to a suspension of 1.7 g of methoxylamine hydrochloride in 40 cm³ of trichloromethane. After stirring for 15 minutes at a temperature close to 20° C., 3.69 g of ethyl 2-(2-chloro-6,7-difluoroquinoline-3-carbonyl)-3-dimethylaminoacrylate are added to the solution obtained and the mixture is stirred for 4 hours and a half at about 20° C. The reaction mixture is concentrated to dryness under reduced pressure (20 kPa) at a temperature close to 50° C. The residue is taken up in 70 cm³ of ethanol and 3.6 g of triethylamine and the mixture is heated for 30 minutes at a temperature close to 75° C. After cooling to about 20° C., the precipitate obtained is drained and washed with 3 times 30 cm³ of ethanol. 2.67 g of 3-ethoxycarbonyl-7,8-difluoro-1-methoxy-4-oxo-1,4-dihydro-benzo[b][1,8]naphthyridine are obtained in the form of a pale yellow solid melting at 266°-268° C.

EXAMPLE 8

A suspension of 8 g of 3-ethoxycarbonyl-7,8-difluoro-1-methyl-4-oxo-1,4-dihydro-benzo[b][1,8]naphthyridine in 80 cm³ of a 17.5% aqueous solution of hydrochloric acid and 80 cm, of acetic acid is heated, with stirring, at a temperature close to 100° C. for one hour and a half. After cooling to about 20° C., the solid is drained and washed with 6 times 100 cm³ of water. After recrystallizing once from 160 cm³ of dimethylformamide, 6.44 g of 7,8-difluoro-1-methyl-4-oxo-1,4-dihydro-benzo[b][1,8]naphthyridine-3-carboxylic acid are obtained in the form of a yellow solid which decomposes at 360° C.

The 3-ethoxycarbonyl-7,8-difluoro-1-methyl-4-oxo-1,4-dihydro-benzo[b][1,8]naphthyridine is prepared in the following manner:

A solution, at about 0° C., of 11.3 g of methylamine in 50 cm³ of ethanol is added in the course of 10 minutes, at between 0° and 5° C. to a stirred suspension of 22.3 g of ethyl 2-(2-chloro-6,7-difluoroquinoline-3-carbonyl)-3-dimethylamino acrylate in 480 cm³ of ethanol, kept at a temperature close to 0° C., the mixture is stirred for 1 hour at between 0° and 5° C., the temperature is allowed to rise to about 25° C. and the mixture is stirred for a further 16 hours at this temperature. The insoluble matter is drained and washed with 3 times 100 cm³ of ethanol and twice 100 cm³ of diethyl ether. After recrystallizing once from 250 cm³ of dimethylformamide, 16 g of 3-ethoxycarbonyl-7,8-difluoro-1-methyl-4-oxo-1,4-dihydro-benzo[b][1,8]naphthyridine are obtained in the form of a yellow solid melting at 323°-324° C.

EXAMPLE 9

A suspension of 4 g of 3-ethoxycarbonyl-7,8,9-trifluoro-1-methyl-4-oxo-1,4-dihydro-benzo[b][1,8]naphthyridine in 30 cm³ of acetic acid and 30 cm³ of 50% hydrochloric acid is heated at a temperature close to 100° C. for 2 hours. After cooling to about 20° C., 100 cm³ of water are added. The precipitate formed is drained, washed with 3 times 50 cm³ of water and recrystallized from 80 cm³ of dimethylformamide 3.4 g of 7,8,9-trifluoro-1-methyl-4-oxo-1,4-dihydro-benzo[b][1,8]naphthyridine-3-carboxylic acid are obtained in the form of a colourless solid melting at 350°–352° C.

The 3-ethoxycarbonyl-7,8,9-trifluoro-1-methyl-4-oxo-1,4-dihydro-benzo[b][1,8]naphthyridine is prepared in the following manner:

A solution, at about 5° C., of 10 g of methylamine in 50 cm³ of ethanol is added in the course of 10 minutes, at between 5° and 10° C., to a stirred suspension of 19.3 g of ethyl 2-(2-chloro-6,7,8-trifluoro-quinoline-3-carbonyl)-3-dimethylaminoacrylate in 150 cm³ of ethanol kept at a temperature close to 5° C., the mixture is stirred for 1 hour at between 5° and 10° C. and the temperature is allowed to rise to about 20° C. 7.6 g of DBU are added to the solution obtained and the mixture is heated at about 30° C. for 1 hour. After cooling to a temperature close to 20° C., the product is drained and washed with twice 100 cm³ of ethanol and twice 100 cm, of diisopropyl ether. 13.4 g of 3-ethoxycarbonyl-7,8,9-trifluoro-1-methyl-4-oxo-1,4-dihydro-benzo[b][1,8]naphthyridine are obtained in the form of a yellow solid melting at 320° C., which is used for the subsequent steps without further purification.

The ethyl 2-(2-chloro-6,7,8-trifluoroquinoline-3-carbonyl)-3-dimethylaminoacrylate can be prepared in the following manner:

A suspension of 26.7 g of ethyl 3-(2-chloro-6,7,8-trifluoro-3-quinolyl)-3-oxopropionate in 270 cm³ of ethyl acetate and 32 cm³ of N,N-dimethylformamide dimethyl acetal is heated at a temperature close to 75° C., with stirring, for 2 hours. The reaction mixture is concentrated to dryness under reduced pressure (20 kPa) at about 50° C. The dry extract is taken up in 175 cm³ of diisopropyl ether, drained and washed with twice 85 cm³ of the same solvent. 19.32 g of ethyl 2-(2-chloro-6,7,8-trifluoroquinoline-3-carbonyl)-3-dimethylaminoacrylate are obtained in the form of an orange solid melting at 118° C., which is used for the subsequent steps without further purification.

The ethyl 3-(2-chloro-6,7,8-trifluoro-3-quinolyl)-3-oxopropionate is prepared in the following manner:

A suspension of 46.3 g of 2-chloro-6,7,8-trifluoroquinoline-3-carboxylic acid in 640 cm³ of trichloromethane and 84 cm³ of thionyl chloride is heated, with stirring, at a temperature close to 60° C. for 6 hours. The solution obtained is concentrated to dryness under reduced pressure (20 kPa) at about 50° C. The dry extract obtained is taken up in 140 cm³ of petroleum ether (40–60), drained and washed with twice 60 cm³ of the same solvent. The 47.61 g of yellow solid obtained are brought into solution in 400 cm³ of tetrahydrofuran. This solution is introduced dropwise, with stirring, in the course of 1 hour and a half, at between 5° and 10° C., into 250 cm³ of a solution of the magnesium chelate of ethyl monomalonate in tetrahydrofuran prepared under the conditions of Example 6. The temperature is allowed to rise to about 20° C. and the mixture is stirred for a further 2 hours under these conditions. The solution obtained is introduced dropwise, with vigorous stirring, in the course of 1 hour, at a temperature close to 5° C., into 1750 cm³ of 0.5N sulphuric acid. The mixture is stirred for a further 2 hours at this temperature and extracted at about 5° C. with 3 times 600 cm³ of diethyl ether. The combined organic phases are washed with 3 times 500 cm³ of water, dried over magnesium sulphate and concentrated under reduced pressure (20 kPa) at a temperature close to 30° C. The dry extract is taken up in a mixture of 135 cm³ of diisopropyl ether and 15 cm³ of n-hexane, drained at about 5° C. and washed with twice 115 cm³ of the same mixture at the same temperature. 47.4 g of ethyl 3-(2-chloro-6,7,8-trifluoro-3-quinolyl)-3-oxopropionate are obtained in the form of a beige solid melting at 78°–80° C., which is used for the subsequent steps without further purification.

The 2-chloro-6,7,8-trifluoroquinoline-3-carboxylic acid is prepared in the following manner:

A solution of 69.65 g of potassium permanganate in 730 cm³ of water is added in the course of 1 hour, while keeping the temperature between 10° and 14° C., to a stirred suspension, cooled to about 10° C., of 45.7 g of 2-chloro-6,7,8-trifluoro-3-formyl-1,4-dihydroquinoline in 585 cm³ of N potassium hydroxide solution. The mixture is stirred for a further 30 minutes at about 10° C. 12 g of sodium dithionite are added and the mixture is stirred for 10 minutes at a temperature close to 10° C. and filtered through diatomaceous silica and the filter cake is washed with 3 times 400 cm³ of water. The filtrate and the washings are combined and 70 cm³ of a 35% aqueous solution of hydrochloric acid are added. The precipitate formed is extracted with 3 times 500 cm³ of ethyl acetate. The combined organic extracts are dried over magnesium sulphate, filtered and concentrated under reduced pressure (20 kPa) at 50° C. The residue is taken up in a mixture of 100 cm³ of diethyl ether and 100 cm³ of diisopropyl ether, drained and washed with 100 cm³ of the same mixture. 46.43 g of 2-chloro-6,7,8-trifluoroquinoline-3-carboxylic acid are obtained in the form of a colourless solid which decomposes at 225°–230° C. and which is used for the subsequent steps without further purification.

The 2-chloro-6,7,8-trifluoro-3-formyl-1,4-dihydroquinoline is prepared in the following manner:

50 cm³ of phosphoryl chloride are added in the course of 40 minutes, with stirring, at between 5° and 10° C., to a mixture of 525 cm³ of trichloromethane and 49 cm³ of dimethylformamide, the mixture is stirred for 15 minutes at this temperature and the temperature is allowed to rise to about 20° C. 46.8 g of 6,7,8-trifluoro-3,4-dihydrocarbostyril are added progressively in the course of 20 minutes, at about 20° C., with vigorous stirring, to the solution obtained. The mixture is stirred for 30 minutes at a temperature close to 20° C., heated to about 60° C. and kept at this temperature for 2 hours and a half. The reaction mixture is concentrated under reduced pressure (20 kPa) at about 50° C. The oily residue is poured into 500 g of ice, with vigorous stirring. 100 g of sodium acetate are added in small fractions in the course of 30 minutes. The suspension obtained is poured in the course of 15 minutes, with vigorous stirring, into 1 liter of water which has previously been heated to about 90° C. and the mixture is stirred for a further 15 minutes at this temperature. The insoluble matter is drained at about 90° C. and washed with 3 times 250 cm³ of water. 47.7 g of 2-chloro-6,7,8-trifluoro-3-formyl-1,4-dihydroquinoline are obtained in the form of a colourless solid which decomposes at 220° C.

The 6,7,8-trifluoro-3,4-dihydrocarbostyril is prepared in the following manner:

24.35 g of 6,7,8-trifluorocarbostyril in suspension in a mixture of 450 cm³ of ethanol and 150 cm³ of dimethylformamide are hydrogenated with stirring, at about 50° C., in the presence of 5 g of Raney nickel under a pressure of 1 atmosphere until the absorption of hydrogen has ceased. The W-2 grade Raney nickel used is washed beforehand with 50 cm³ of an aqueous 2% acetic acid solution, twice 50 cm³ of water and 3 times 50 cm³ of ethanol. 250 cm³ of dimethylformamide are added to the reaction mixture and the mixture is filtered at about 50° C. through diatomaceous silica. The filtrate is concentrated under reduced pressure (20 kpa) at about 70° C. The dry extract is taken up in 150 cm³ of water, drained and washed with twice 50 cm³ of water. 23.6 g of 6,7,8-trifluoro-3,4-dihydrocarbostyril are obtained in the form of a light beige solid melting at 217° C., which is used for the subsequent steps without further purification.

The 6,7,8-trifluorocarbostyril is prepared in the following manner:

60.83 g of 4-chloro-6,7,8-trifluorocarbostyril in suspension in 520 cm³ of acetic acid and 38.15 cm³ of triethylamine are hydrogenated under a pressure of 1 atmosphere in the presence of 5.25 g of 10% palladium-on-charcoal until the absorption of hydrogen has ceased, at a temperature close to 25° C. The reaction mixture is then heated to about 40° C. and filtered at this temperature through diatomaceous silica for filtration. The filtrate is concentrated under reduced pressure (20 kPa) at a temperature close to 50° C. The dry extract is taken up in 400 cm³ of water; the insoluble matter is drained and washed with 4 times 170 cm³ of water, twice 110 cm³ of ethanol and twice 100 cm³ of diisopropyl ether. 48.35 g of 6,7,8-trifluorocarbostyril are obtained in the form of a colourless solid which sublimes at 288° C. and which is used for the subsequent steps without further purification.

The 4-chloro-6,7,8-trifluorocarbostyril is prepared in the following manner:

A suspension of 70.4 g of 4-chloro-2-ethoxy-6,7,8-trifluoroquinoline in 170 cm³ of a 35% aqueous solution of hydrochloric acid, 420 cm³ of acetic acid and 250 cm³ of water is heated, with stirring, at a temperature close to 100° C. for 2 hours and a half. After cooling to about 20° C., the reaction mixture is poured into 1,100 cm³ of water at about 5° C., the mixture is stirred for 15 minutes at this temperature and the insoluble matter is then drained and washed with 3 times 220 cm³ of water. 61 g of 4-chloro-6,7,8-trifluorocarbostyril are obtained in the form of a cream solid melting at 213° C., which is used for the subsequent steps without further purification.

The 4-chloro-2-ethoxy-6,7,8-trifluoroquinoline is prepared in the following manner:

A suspension of 69.5 g of 2-ethoxy-6,7,8-trifluoro-4-hydroxyquinoline in 430 cm³ of phosphoryl chloride is heated, with stirring, at a temperature close to 100° C. for 30 minutes. The solution obtained is concentrated under reduced pressure (20 kPa) at about 60° C. until the volume is 100 cm³. The residue is taken up in 750 cm³ of ethyl acetate; the solution obtained is poured, with stirring, in the course of 10 minutes into a mixture of 400 cm³ of water and 200 g of ice and the mixture is stirred under these conditions for 30 minutes. After separating off the organic extract, the aqueous phase is extracted again with twice 250 cm³ of ethyl acetate. The combined organic extracts are washed with 3 times 250 cm³ of water, dried over magnesium sulphate and concentrated under reduced pressure (20 kPa) at about 40° C. The oily residue obtained is taken up in 370 cm³ of petroleum ether (40–60). After filtering through diatomaceous silica, the filtrate is concentrated to dryness under reduced pressure (20 kPa) at about 30° C. 70.7 g of 4-chloro-2-ethoxy-6,7,8-trifluoroquinoline are obtained in the form of a beige solid melting at 45° C., which is used for the subsequent steps without further purification.

The 2-ethoxy-6,7,8-trifluoro-4-hydroxyquinoline can be prepared in the following manner:

A solution of 122 g of 2,3,4-trifluoro-N-[(1'-ethoxy-2'-ethoxycarbonyl)ethylidene]-aniline in 120 cm³ of phenyl oxide is introduced dropwise, in the course of 25 minutes, with stirring, into 600 cm³ of phenyl oxide at a temperature close to 250° C. while removing the ethanol formed by distillation. After stirring for 15 minutes at this temperature, the solution is cooled to about 20° C. and 750 cm³ of n-hexane are added. The precipitate formed is drained and washed 3 times with 200 cm³ of n-hexane. 69.5 g of 2-ethoxy-6,7,8-trifluoro-4-hydroxyquinoline are obtained in the form of a beige solid melting at 171° C., which is used for the subsequent steps without further purification.

The 2,3,4-trifluoro-N-[(1'-ethoxy-2'-ethoxycarbonyl)ethylidene]-aniline can be prepared in the following manner:

58.8 g of 2,3,4-trifluoroaniline are added in a single amount, with stirring, to a solution of 90 g of 2-ethoxycarbonyl-1-ethoxy-ethylideneamine hydrochloride in 820 cm³ of ethanol. After stirring for 48 hours at a temperature close to 20° C., the suspension obtained is filtered; the filtrate is concentrated under reduced pressure (20 kPa) at a temperature close to 50° C. The oily residue is taken up in 250 cm³ of water. The mixture obtained is extracted with 3 times 200 cm³ of diethyl ether. The combined organic extracts are washed with 4 times 150 cm³, of water, dried over magnesium sulphate and concentrated under reduced pressure (20 kPa) at about 30° C. 122 g of 2,3,4-trifluoro-N-[(1'-ethoxy-2'-ethoxycarbonyl)ethylidene]-aniline are obtained in the form of a yellow oil which is used for the subsequent steps without further purification.

The 2-ethoxycarbonyl-1-ethoxy-ethylideneamine hydrochloride was prepared by the method described by A. Pinner, et al., Ber. Dtsch. Chem. Ges., 28, 478 (1895).

EXAMPLE 10

The 6,7,8-trifluoro-1-methoxy-4-oxo-1,4-dihydrobenzo[b][1,8]naphthyridine-3-carboxylic acid was prepared under the conditions of Example 9 but starting from 9 g of 3-ethoxycarbonyl-6,7,8-trifluoro-1-methoxy-4-oxo-1,4-dihydro-benzo[b][1,8]naphthyridine. 7.7 g of 6,7,8-trifluoro-1-methoxy-4-oxo-1,4-dihydro-benzo[b][1,8]naphthyridine-3-carboxylic acid are obtained in the form of a beige solid melting at 322° C.

The 3-ethoxycarbonyl-6,7,8-trifluoro-1-methoxy- 4-oxo-1,4-dihydro-benzo[b][1,8]naphthyridine was prepared under the following conditions:

8.7 cm³ of triethylamine are added to a suspension of 5.1 g of methylhydroxylamine hydrochloride in 120 cm³ of trichloromethane. 7.8 g of ethyl 2-(2-chloro-6,7,8-trifluoroquinoline-3-carbonyl)-3-dimethylaminoacrylate are added, at about 20° C., to the solution obtained. After stirring for 2 hours at this temperature, the solution is concentrated to dryness under reduced pressure (20 kPa) at about 50° C. The residue obtained is taken up in 150 cm³ of ethanol and 10 cm³ of triethylamine and the mixture is heated, with stirring, for 30 minutes. After cooling to about 20° C., the insoluble matter is drained and washed with 3 times 50 cm³ of ethanol and twice 50 cm³ of diisopropyl ether. After recrystallizing from 120 cm³ of dimethylformamide, 9 g of 3-ethoxycarbonyl-6,7,8-trifluoro-1-methoxy-4-oxo-1,4-dihydro-benzo[b][1,8]naphthyridine are obtained in the form of a yellow solid melting at 298°–300° C.

EXAMPLE 11

Carrying out the reaction under the conditions of Example 9, but starting from 1.8 g of 1-cyclopropyl-3-ethoxycarbonyl-7,8,9-trifluoro-4-oxo-1,4-dihydro-benzo[b][1,8]naphthyridine, 1.1 g of 1-cyclopropyl7,8,9-trifluoro-4-oxo-1,4-dihydro-benzo-[b][1,8]naphthyridine-3-carboxylic acid are obtained in the form of a yellow solid melting at 304° C.

The 1-cyclopropyl-3-ethoxycarbonyl-7,8,9-trifluoro-4-oxo-1,4-dihydro-benzo[b][1,8]naphthyridine can be prepared in the following manner:

4.12 g of cyclopropylamine are added in the course of 5 minutes to a solution of 7 g of ethyl 2-(2-chloro-6,7,8-trifluoroquinoline-3-carbonyl)-3-dimethylamino acrylate in 100 cm³ of trichloromethane kept at a temperature close to 20° C. and the mixture is stirred for a further 4 hours at this temperature. The reaction mixture is concentrated under reduced pressure (20 kPa) 100 cm³ of ethanol and 3 g of DBU. The mixture is heated to 80° C. and kept at this temperature, with stirring, for 1 hour and a half. After cooling to about 20° C., the insoluble matter is drained and washed with twice 30 cm³ of ethanol and twice 30 cm³ of diisopropyl ether. 4.5 g of 1-cyclopropyl-3-ethoxycarbonyl-7,8,9-trifluoro-4-oxo-1,4-dihydro-benzo[b][1,8]naphthyridine are obtained in the form of a colourless solid melting at 260° C.

EXAMPLE 12

A suspension of 6 g of 8-chloro-3-ethoxycarbonyl-1-ethoxymethyl-7-fluoro-4-oxo-1,4-dihydro-benzo[b][1,8-]naphthyridine in 120 cm³ of water, 120 cm³ of ethanol and 47.5 cm³ of 2N aqueous potassium hydroxide solution is heated, with stirring, at a temperature close to 75° C. for 2 hours and a half. A small amount of insoluble matter is removed by filtering at the same temperature. After cooling to about 20° C., 6 cm³ of acetic acid are added to the filtrate. The precipitate obtained is drained, washed with 3 times 20 cm³ of water and recrystallized from 60 cm³ of dimethylformamide. 4 g of 8-chloro-1-ethoxymethyl-7-fluoro-4-oxo-1,4-dihydro-benzo[b][1,8]naphthyridine-3-carboxylic acid are obtained in the form of a yellow solid which decomposes at 285° C.

The 8-chloro-3-ethoxycarbonyl-1-ethoxymethyl-7-fluoro-4-oxo-1,4-dihydro-benzo[b][1,8]naphthyridine is prepared in the following manner:

A suspension of 6 g of 8-chloro-3-ethoxycarbonyl-7-fluoro-4-oxo-1,4-dihydro-benzo[b][1,8]naphthyridine and 5.16 g of potassium carbonate in 120 cm³ of dimethylformamide is heated at a temperature close to 110° C. for 1 hour. After cooling to about 15° C., 5.44 cm³ of chloromethyl ethyl ether are added and the mixture is stirred for 5 hours at between 15° and 20° C. The reaction mixture is concentrated to dryness under reduced pressure (20 kPa) at about 60° C. The residue is taken up in 3 times 150 cm³ of trichloromethane. The combined organic extracts are filtered in order to remove the insoluble matter. The filtrate is dried over magnesium sulphate and concentrated under reduced pressure (20 kPa) at about 40° C. The residue is recrystallized from 55 cm³ of dimethylformamide. 5.6 g of 8-chloro-3-ethoxycarbonyl-1-ethoxymethyl-7-fluoro-4-oxo-1,4-dihydro-benzo[b][1,8]naphthyridine are obtained in the form of a beige solid melting at 261° C.

The 8-chloro-3-ethoxycarbonyl-7-fluoro-4-oxo-1,4-dihydro-benzo[b][1,8]naphthyridine was prepared in the following manner:

A mixture of 11.3 g of ethyl 2-(2,7-dichloro-6-fluoroquinoline-3-carbonyl)-3-dimethylaminoacrylate and 5.65 g of 3-amino-1,2,4-triazine in 60 cm³ of trichloromethane is stirred for 16 hours at a temperature close to 20° C. The reaction mixture is concentrated to dryness under reduced pressure (20 kPa) at a temperature close to 30° C. The residue is taken up in 60 cm³ of ethanol and 5.6 g of DBU and the mixture is heated at a temperature close to 75° C. for 20 hours. After cooling to 20° C., the insoluble matter is drained and washed with twice 40 cm³ of ethanol. 6.1 g of 8-chloro-3-ethoxycarbonyl-7-fluoro-4-oxo-1,4-dihydro-benzo[b][1,8-]naphthyridine are obtained in the form of a brown solid which decomposes at 378°–380° C. and is used for the subsequent steps without further purification.

EXAMPLE 13

A suspension of 5.75 g of 8-chloro-3-ethoxycarbonyl-7-fluoro-4-oxo-1,4-dihydro-benzo[b][1,8]naphthyridine in 60 cm³ of 17.5% hydrochloric acid is heated, with stirring, at a temperature close to 100° C. for 30 minutes. After cooling to about 20° C., the insoluble matter is drained and washed with 3 times 20 cm³ of ethanol and 3 times 20 cm³ of diethyl ether. 3.05 g of 8-chloro-7-fluoro- 4-oxo-1,4-dihydro-benzo[b][1,8]naphthyridine-3-carboxylic acid are obtained in the form of a beige solid which decomposes at 416° C.

EXAMPLE 14

A suspension of 8 g of 3-ethoxycarbonyl-1-ethyl-7,8-difluoro-4-oxo-1,4-dihydro-benzo[b][1,8]naphthyridine in 80 cm³ of 17.5% hydrochloric acid and 80 cm³ of acetic acid is heated, with stirring, at a temperature close to 100 hour and 30 minutes. After cooling to about 20° C., the insoluble matter is drained, washed with 3 times 20 cm³ of water and recrystallized from 50 cm³ of dimethylformamide. 6.3 g of 1-ethyl-7,8-difluoro-4-oxo-1,4-dihydro-benzo[b][1,8]naphthyridine-3-carboxylic acid are obtained in the form of a yellow solid melting at 330° C.

The 3-ethoxycarbonyl-1-ethyl-7,8-difluoro-4-oxo-1,4-dihydro-benzo[b][1,8]naphthyridine was prepared under the following conditions:

A solution, at about 2° C., of 14.6 g of ethylamine in 200 cm³ of ethanol is added, in the course of 10 minutes, at between 2° and 5° C., with stirring, to a suspension of 20 g of ethyl 2-(2-chloro-6,7-difluoroquinoline-3-carbonyl)-3-dimethylamino acrylate in 200 cm³ of ethanol at about 2° C., the mixture is stirred for a further 40 minutes at between 2° and 5° C. and the temperature is then allowed to rise to about 20° C. in the course of 2 hours. After 24 hours at about 20° C., the insoluble matter is drained and washed with twice 30 cm³ of ethanol and twice 50 cm³ of diisopropyl ether. 16.35 g of 3-ethoxycarbonyl-1-ethyl-7,8-difluoro-4-oxo-1,4-dihydro-benzo[b][1,8]naphthyridine are obtained in the form of a beige solid melting at

EXAMPLE 15

8-Chloro-7-fluoro-1-(2-fluoroethyl)-4-oxo-1,4-dihydro-benzo[b][1,8]naphthyridine-3-carboxylic acid is prepared under the conditions of Example 9 but starting from 2.2 g of 8-chloro-3-ethoxycarbonyl-7-fluoro-1-(2-fluoroethyl)-4-oxo-1,4-dihydro-benzo[b][1,8]naphthyridine. After recrystallizing twice from 10 cm³ of dimethylformamide each time, 1.4 g of 8-chloro-7-fluoro-1-(2-fluoroethyl)-4-oxo-1,4-dihydro-benzo[b][1,8]naphthyridine-3-carboxylic acid are obtained in the form of a yellow solid melting at 310° C.

8-Chloro-3-ethoxycarbonyl-7-fluoro-1-(2-fluoroethyl)-4-oxo-1,4-dihydro-benzo[b][1,8]naphthyridine is prepared in the following manner:

2.7 cm³ of triethylamine are added to a suspension of 1.9 g of 2-fluoroethylamine hydrochloride in 25 cm³ of trichloromethane. 3.5 g of ethyl 2-(2,7-dichloro-6-fluoroquinoline-3-carbonyl)-3-dimethylaminoacrylate are added to the solution obtained at about 20° C. After stirring at this temperature for 16 hours, the solution is concentrated to dryness under reduced pressure (20 kPa) at about 50° C. The residue is taken up in 20 cm³ of ethanol and 3 cm³ of triethylamine and heated at about 75° C., with stirring, for 2 hours. After cooling to about 20° C. the insoluble matter is drained and washed with twice 10 cm³ of ethanol and twice 10 cm³ of diisopropyl ether. 1.9 g of 8-chloro-3-ethoxycarbonyl-7-fluoro-1-(2-fluoroethyl)-4-oxo-1,4-dihydro-benzo[b][1,8]naphthyridine are obtained in the form of a yellow solid melting at 268° C., which is used for the subsequent step without further purification Tho products according to the invention can be used under the conditions described below by way of example:

REFERENCE EXAMPLE 1

A suspension of 3.5 g of 8-chloro-7-fluoro-1-methyl-4-oxo-1,4-dihydro-benzo[b][1,8]naphthyridine-3-carboxylic acid and 4.6 g of 2-methylpiperazine in 40 cm³ of pyridine is heated at a temperature close to 115° C., with stirring, for 13 hours. The reaction mixture is concentrated to dryness under reduced pressure (20 kPa) at 60° C. The residue is twice taken up with 30 cm³ of ethanol and concentrated under reduced pressure under the above conditions. The solid obtained is taken up in 60 cm³ of water and 10 cm³ of 30% aqueous potassium hydroxide solution. The aqueous phase is washed with twice 100 cm³ of trichloromethane, 10.28 g of methanesulphonic acid are added and the aqueous phase is again washed with twice 100 cm³ of trichloromethane. 10 cm³ of 30% aqueous potassium hydroxide solution are added. The precipitate formed is drained and washed with 3 times 10 cm³ of water and twice 10 cm³ of ethanol. 2.7 g of 7-fluoro-1-methyl-8-(3-methyl-1-piperazinyl)-4-oxo-1,4-dihydro-benzo[b][1,8]naphthyridine-3-carboxylic acid are obtained in the form of a yellow solid melting at 360°–363° C.

REFERENCE EXAMPLE 2

7-Fluoro-1-methyl-4-oxo-8-(1-piperazinyl)-1,4-dihydro-benzo[b][1,8]naphthyridine-3-carboxylic acid is prepared under the conditions of Reference Example 1 but starting from 10 g of 8-chloro-7-fluoro-1-methyl-4-oxo-1,4-dihydro-benzo[b][1,8]naphthyridine-3-carboxylic acid and 28 g of piperazine in 100 cm³ of pyridine. 5.5 g of 7-fluoro-1-methyl-4-oxo-8-(1-piperazinyl)-1,4-dihydro-benzo[b][1,8]naphthyridine-3-carboxylic acid hemihydrate are obtained in the form of a yellow solid melting at 370°–375° C.

REFERENCE EXAMPLE 3

7-Fluoro-1-methyl-8-(4-methyl-1-piperazinyl)-4-oxo-1,4-dihydro-benzo[b][1,8]naphthyridine-3-carboxylic acid is prepared under conditions analogous to Reference Example 1 but starting from 5 g of 8-chloro-7-fluoro-1-methyl-4-oxo-1,4-dihydro-benzo[b][1,8]naphthyridine-3-carboxylic acid and 16 g of 1-methylpiperazine in 50 cm³ of pyridine. After concentrating the reaction mixture under reduced pressure, 25 cm³ of acetic acid are added to the residue, which is suspended in 100 cm³ of water. A very small amount of insoluble matter is removed by filtration through diatomaceous silica for filtration. 200 cm³ of 3N aqueous potassium hydroxide solution are added to the filtrate and a very small amount of insoluble matter is again removed by filtration through diatomaceous silica for filtration. 5 cm³ of acetic acid are added to the filtrate. The precipitate formed is drained and washed with 3 times 50 cm³ of water. After recrystallizing twice from 17 cm³ of dimethylformamide each time, 3.2 g of 7-fluoro-1-methyl-8-(4-methyl-1-piperazinyl)-4-oxo-1,4-dihydro-benzo[b][1,8]naphthyridine-3-carboxylic acid are obtained in the form of a yellow solid melting at 356° C.

REFERENCE EXAMPLE 4

8-(4-Ethyl-1-piperazinyl)-7-fluoro-1-methyl-4-oxo-1,4-dihydro-benzo[b][1,8]naphthyridine-3-carboxylic acid is prepared under the conditions described below in Reference Example 5 but starting from 1.85 g of 8-chloro-7-fluoro-1-methyl-4-oxo-1,4-dihydro-benzo[b][1,8]naphthyridine-3-carboxylic acid and 2.75 g of 1-ethylpiperazine in 20 cm³ of pyridine 1.3 g of 8-(4-ethyl-1-piperazinyl)-7-fluoro-1-methyl-4-oxo-1,4-dihydro-benzo[b][1,8]naphthyridine-3-carboxylic acid are obtained in the form of a yellow solid melting at 285°–286° C.

REFERENCE EXAMPLE 5

7-Fluoro-8-[4-(2-hydroxyethyl)-1-piperazinyl]-1-methyl-4-oxo-1,4-dihydro-benzo[b][1,8]naphthyridine-3-carboxylic acid is prepared under the conditions of Reference Example 1 but starting from 1.6 g of 8-chloro-7-fluoro-1-methyl-4-oxo-1,4-dihydro-benzo[b][1,8]naphthyridine-3-carboxylic acid and 6.8 g of 1-(2-hydroxyethyl)-piperazine in 16 cm³ of pyridine. After concentrating the reaction mixture to dryness under reduced pressure, the residue is taken up in 50 cm³ of water. The mixture is brought to pH 6.9 by adding 0.4 cm³ of acetic acid. The precipitate obtained is drained, washed with twice 10 cm³ of water and recrystallized twice from 10 cm³ of dimethylformamide. 1.1 g of 7-fluoro-8-[4-(2-hydroxyethyl)-1-piperazinyl]-1-methyl-4-oxo-1,4-dihydro-benzo[b][1,8]naphthyridine-3-carboxylic acid are obtained in the form of a yellow solid melting at 275°–276° C.

REFERENCE EXAMPLE 6

8-(3,5-Dimethyl-1-piperazinyl)-7-fluoro-1-methyl-4-oxo-1,4-dihydro-benzo[b][1,8]naphthyridine-3-carboxylic acid is prepared under the conditions of Reference Example 3 but starting from 1.7 g of 8-chloro-7-fluoro-1-methyl-4-oxo-1,4-dihydro-benzo[b][1,8]naphthyridine-3-carboxylic acid and 2.5 g of 2,6-dimethylpiperazine in 20 cm³ of pyridine. 1.1 g of 8-(3,5-dimethyl-1'-piperazinyl)-7-fluoro-1-methyl-4-oxo-1,4-dihydro-ben-

REFERENCE EXAMPLE 7

1-Ethyl-7-fluoro-8-(1-piperazinyl)-4-oxo-1,4-dihydro-benzo[b][1,8]naphthyridine-3-carboxylic acid is prepared under the conditions of Reference Example 5, but starting from 1.6 g of 8-chloro-1-ethyl-7-fluoro-4-oxo-1,4-dihydro-benzo[b][1,8]naphthyridine-3-carboxylic acid and 4.3 g of piperazine in 20 cm³ of pyridine. After recrystallizing 3 times from, in total, 300 cm³ of dimethylformamide, 0.94 g of 1-ethyl-7-fluoro-8-(1-piperazinyl)-4-oxo-1,4-dihydro-benzo[b][1,8]naphthyridine-3-carboxylic acid trihydrate is obtained in the form of a yellow solid melting at 320°–322° C.

REFERENCE EXAMPLE 8

1-Ethyl-7-fluoro-8-(4-methyl-1-piperazinyl)-4-oxo-1,4-dihydro-benzo[b][1,8]naphthyridine-3-carboxylic acid is prepared under the conditions of Reference Example 5 but starting from 1.6 g of 8-chloro-1-ethyl-7-fluoro-4-oxo-1,4-dihydro-benzo[b][1,8]naphthyridine-3-carboxylic acid and 4.5 g of 4-methylpiperazine in 16 cm³ of pyridine After recrystallizing 4 times from, in total, 120 cm³ of dimethylformamide, 1.2 g of 1-ethyl-7-fluoro-8-(4-methyl-1-piperazinyl)-4-oxo-1,4-dihydro-benzo[b][1,8]naphthyridine-3-carboxylic acid are obtained in the form of a yellow solid melting at 285°–286° C. solvated by 1% of water.

REFERENCE EXAMPLE 9

1-Ethyl-7-fluoro-8-(3-methyl-1-piperazinyl)-4-oxo-1,4-dihydro-benzo[b][1,8]naphthyridine-3-carboxylic acid is prepared under the conditions of Reference Example 1 but starting from 2.1 g of 8-chloro-1-ethyl-7-fluoro-4-oxo-1,4-dihydro-benzo[b][1,8]naphthyridine-3-carboxylic acid, 20 cm³ of pyridine and 2.4 g of 2-methylpiperazine.

After taking up in ethanol and concentrating to dryness under reduced pressure (20 kPa at 50° C.), the solid residue is taken up in 20 cm³ of water and 10 cm³ of 2N potassium hydroxide solution. The aqueous solution obtained is washed with twice 20 cm³ of trichloromethane, 10 cm³ of acetic acid are added and the mixture is again washed with twice 40 cm³ of trichloromethane. 23 cm³ of 4.5N potassium hydroxide solution are added and the suspension obtained is heated to a temperature close to 90° C. After cooling to a temperature close to 20° C., the precipitate is drained and washed with 3 times 10 cm³ of water and twice 10 cm³ of ethanol. After recrystallizing twice from 120 cm³ of dimethylformamide each time, 1.7 g of 1-ethyl-7-fluoro-8-(3-methyl-1-piperazinyl)-4-oxo-1,4-dihydro-benzo[b][1,8]naphthyridine-3-carboxylic acid are obtained in the form of a yellow solid melting at 310°–312° C.

REFERENCE EXAMPLE 10

1-Ethyl-8-(4-ethyl-1-piperazinyl)-7-fluoro-4-oxo-1,4-dihydro-benzo[b][1,8]naphthyridine-3-carboxylic acid is prepared under the conditions of Reference Example 5 but starting from 1.6 g of 8-chloro-1-ethyl-7-fluoro-4-oxo-1,4-dihydro-benzo[b][1,8]naphthyridine-3-carboxylic acid and 2.3 g of 1-ethylpiperazine in 16 cm³ of pyridine. 1.4 g of 1-ethyl-8-(4-ethyl-1-piperazinyl)-7-fluoro-4-oxo-1,4-dihydro-benzo[b][1,8]naphthyridine-3-carboxylic acid are obtained in the form of a yellow solid melting at 287°–288° C., solvated by 1.6% of water.

REFERENCE EXAMPLE 11

1-Ethyl-7-fluoro-8-[4-(2-hydroxyethyl)-1-piperazinyl]-4-oxo-1,4-dihydro-benzo[b][1,8]naphthyridine-3-carboxylic acid is prepared under the conditions of Reference Example 5 but starting from 1.6 g of 8-chloro-1-ethyl-7-fluoro-4-oxo-1,4-dihydro-benzo[b][1,8]naphthyridine-3-carboxylic acid and 2.6 g of 1-(2-hydroxyethyl)-piperazine in 16 cm³ of pyridine. 1.3 g of 1-ethyl-7-fluoro-8-[4-(2-hydroxyethyl)-1-piperazinyl]-4-oxo-1,4-dihydro-benzo[b][1,8]naphthyridine-3-carboxylic acid are obtained in the form of a yellow solid melting at 264°–265° C.

REFERENCE EXAMPLE 12

7-Fluoro-1-methylamino-4-oxo-8-(1-piperazinyl)-1,4-dihydro-benzo[b][1,8]naphthyridine-3-carboxylic acid is prepared under the conditions of Reference Example 5 but starting from 2.25 g of 8-chloro-7-fluoro-1-methylamino-4-oxo-1,4-dihydro-benzo[b][1,8]naphthyridine-3-carboxylic acid and 2.4 g of piperazine in 30 cm³ of pyridine. After recrystallizing 3 times from, in total, 400 cm³ of dimethylformamide, 0.82 g of 7-fluoro-1-methylamino-4-oxo-8-(1-piperazinyl)-1,4-dihydro-benzo[b][1,8]naphthyridine-3-carboxylic acid is obtained in the form of a deep yellow solid melting at 322°–324° C., solvated by 13.6% of dimethylformamide.

REFERENCE EXAMPLE 13

7-Fluoro-1-methylamino-8-(4-methyl-1-piperazinyl)-4-oxo-1,4-dihydro-benzo[b][1,8]naphthyridine-3-carboxylic acid is prepared under conditions analogous to Reference Example 1 but starting from 1.93 g of 8-chloro-7-fluoro-1-methylamino-4-oxo-1,4-dihydro-benzo[b][1,8]naphthyridine-3-carboxylic acid, 2.4 g of 1-methylpiperazine and 20 cm³ of pyridine After recrystallizing twice from 15 cm³ of dimethylformamide each time, 0.9 g of 7-fluoro-1-methylamino-8-(4-methyl-1-piperazinyl)-4-oxo-1,4-dihydro-benzo[b][1,8]naphthyridine-3-carboxylic acid is obtained in the form of a yellow solid melting at 263°–264° C.

REFERENCE EXAMPLE 14

7-Fluoro-1-methylamino-8-(3-methyl-1-piperazinyl)-4-oxo-1,4-dihydro-benzo[b][1,8]naphthyridine-3-carboxylic acid is prepared under the conditions of Reference Example 5 but starting from 3.2 g of 8-chloro-7-fluoro-1-methylamino-4-oxo-1,4-dihydro-benzo[b][1,8-]naphthyridine-3-carboxylic acid and 4 g of 2-methylpiperazine in 40 cm³ of pyridine. The crude product obtained is taken up in 30 cm³ of water and 7 cm³ of 2N aqueous potassium hydroxide solution. A very small amount of insoluble matter is removed by filtration through diatomaceous silica. The filtrate is washed with twice 20 cm³ of diethyl ether and the product is then precipitated by adding 3.5 cm³ of 4N methanesulphonic acid. The precipitate obtained is drained and washed with 3 times 20 cm³ of water and 3 times 20 cm³ of ethanol 2.2 g of 7-fluoro-1-methylamino-8-(3-methyl-1-piperazinyl)-4-oxo-1,4-dihydro-benzo[b][1,8]naphthyridine-3-carboxylic acid are obtained in the form of a deep yellow solid melting at 343°–345° C., solvated by 3.7% of water.

REFERENCE EXAMPLE 15

1-Cyclopropyl-7-fluoro-4-oxo-8-(1-piperazinyl)-1,4-dihydro-benzo[b][1,8]naphthyridine-3-carboxylic acid is prepared under the conditions of Reference Example 5 but starting from 1 g of 8-chloro-1-cyclopropyl-7-fluoro-4-oxo-1,4-dihydro-benzo[b][1,8]naphthyridine-3-carboxylic acid and 2.6 g of piperazine in 10 cm³ of pyridine. 0.6 g of 1-cyclopropyl-7-fluoro-4-oxo-8-(1-piperazinyl)-1,4-dihydro-benzo[b][1,8]naphthyridine-3-carboxylic acid dihydrate is obtained in the form of a yellow solid melting at 342°–343° C.

REFERENCE EXAMPLE 16

1-Cyclopropyl-7-fluoro-8-(4-methyl-1-piperazinyl)-4-oxo-1,4-dihydro-benzo[b][1,8]naphthyridine-3-carboxylic acid is prepared under the conditions of Reference Example 5 but starting from 1 g of 8-chloro-1-cyclopropyl-7-fluoro-4-oxo-1,4-dihydro-benzo[b][1,8]naphthyridine-3-carboxylic acid and 3 g of 1-methylpiperazine in 10 cm³ of pyridine. After recrystallizing from 10 cm³ of dimethylformamide, 0.63 g of 1-cyclopropyl-7-fluoro-8-(4-methyl-1-piperazinyl)-4-oxo-1,4-dihydro-benzo[b][1,8]naphthyridine-3-carboxylic acid is obtained in the form of a yellow solid melting at 250° C.

REFERENCE EXAMPLE 17

1-Cyclopropyl-7-fluoro-8-(3-methyl-1-piperazinyl)-4-oxo-1,4-dihydro-benzo[b][1,8]naphthyridine-3-carboxylic acid is prepared under the conditions of Reference Example 1 but starting from 1 g of 8-chloro-1-cyclopropyl-7-fluoro-4-oxo-1,4-dihydro-benzo[b][1,8]naphthyridine-3-carboxylic acid and 3 g of 2-methylpiperazine in 10 cm³ of pyridine. The pure product is obtained after a supplementary purification by recrystallization from 200 cm³ of dimethylformamide. 0.5 g of 1-cyclopropyl-7-fluoro-8-(3-methyl-1-piperazinyl)-4-oxo-1,4-dihydro-benzo[b][1,8]naphthyridine-3-carboxylic acid hemihydrate is obtained in the form of a yellow solid melting at 343° C.

REFERENCE EXAMPLE 18

1-Cyclopropyl-8-(4-ethyl-1-piperazinyl)-7-fluoro-4-oxo-1,4-dihydro-benzo[b][1,8]naphthyridine-3-carboxylic acid is prepared under the conditions of Reference Example 5 but starting from 2 g of 8-chloro-1-cyclopropyl-7-fluoro-4-oxo-1,4-dihydro-benzo[b][1,8]naphthyridine-3-carboxylic acid and 2.74 g of 1-ethyl-piperazine in 20 cm³ of pyridine. The pure product is isolated after a first recrystallization from 105 cm³ of ethanol containing 25% of dimethylformamide followed by a second recrystallization from 75 cm³ of ethanol containing 50% of dimethylformamide. 0.67 g of 1-cyclopropyl-8-(4-ethyl-1-piperazinyl)-7-fluoro-4-oxo-1,4-dihydro-benzo[b][1,8]naphthyridine-3-carboxylic acid is obtained in the form of a yellow-green solid melting at 254° C.

REFERENCE EXAMPLE 19

1-Cyclopropyl-7-fluoro-8-[4-(2-hydroxyethyl)-1-piperazinyl]-4-oxo-1,4-dihydro-benzo[b][1,8]naphthyridine-3-carboxylic acid is prepared under conditions analogous to Reference Example 5 but starting from 4 g of 8-chloro-1-cyclopropyl-7-fluoro-4-oxo-1,4-dihydro-benzo[b][1,8]naphthyridine-3-carboxylic acid and 6.2 g of 1-(2-hydroxyethyl)-piperazine in 40 cm³ of pyridine. The reaction mixture is heated for 22 hours at a temperature close to 115° C. The pure product is isolated after recrystallizing 3 times from 3 times 200 cm³ of ethanol containing 10% of dimethylformamide each time. 0.94 g of 1-cyclopropyl-7-fluoro-8-[4-(2-hydroxyethyl)-1-piperazinyl]-4-oxo-1,4-dihydro-benzo[b][1,8]naphthyridine-3-carboxylic acid is obtained in the form of a yellow solid melting at 255° C.

REFERENCE EXAMPLE 20

7-Fluoro-4-oxo-8-(1-piperazinyl)-1-tert.-butyl-1,4-dihydro-benzo[b][1,8]naphthyridine-3-carboxylic acid is prepared under the conditions of Reference Example 5 but starting from 1.7 g of 8-chloro-7-fluoro-4-oxo-1-tert.-butyl-1,4-dihydro-benzo[b][1,8]naphthyridine-3-carboxylic acid and 4.3 g of piperazine in 20 cm³ of pyridine. The pure product is obtained after a single recrystallization from 20 cm³ of dimethylformamide. 1.25 g of 7-fluoro-4-oxo-8-(1-piperazinyl)-1-tert.-butyl-1,4-dihydro-benzo[b][1,8]naphthyridine-3-carboxylic acid are isolated in the form of a yellow solid melting at 90° C., solvated by 4.5% of water.

REFERENCE EXAMPLE 21

A solution of 1.15 g of 7-fluoro-1-methyl-8-(3-methyl-1-piperazinyl)-4-oxo-1,4-dihydro-benzo[b][1,8]naphthyridine-3-carboxylic acid in 1.35 cm³ of 98% formic acid and 3.25 cm³ of a 30% aqueous solution of formaldehyde is heated at a temperature close to 100° C. for 2 hours. The reaction mixture is concentrated under reduced pressure (20 kPa) at 50° C. and 5 cm³ of water are then added, the solution obtained is brought to pH 7 by adding 0.5 cm³ of 2N aqueous potassium hydroxide solution and heated at a temperature close to 100° C. for 2 minutes. The product, which crystallizes, is drained at 20° C. and washed with twice 10 cm³ of water. The crude product obtained is recrystallized twice from 10 cm³ of dimethylformamide each time. 0.55 g of 8-(3,4-dimethyl-1-piperazinyl)-7-fluoro-1-methyl-4-oxo-1,4-dihydro-benzo[b][1,8]naphthyridine-3-carboxylic acid is obtained in the form of a yellow solid melting at 306°–308° C.

REFERENCE EXAMPLE 22

8-(3,4-Dimethyl-1-piperazinyl)-1-ethyl-7-fluoro-4-oxo-1,4-dihydro-benzo[b][1,8]naphthyridine-3-carboxylic acid is prepared under the conditions of Reference Example 21 but starting from 2.3 g of 1-ethyl-7-fluoro-8-(3-methyl-1-piperazinyl)-4-oxo-1,4-dihydro-benzo[b][1,8]naphthyridine-3-carboxylic acid, 2.26 cm³ of 98% formic acid and 5.6 cm³ of a 30% aqueous solution of formaldehyde. 1.75 g of 8-(3,4-dimethyl-1-piperazinyl)-1-ethyl-7-fluoro-4-oxo-1,4-dihydro-benzo[b][1,8]naphthyridine-3-carboxylic acid are obtained in the form of a yellow solid melting at 293°–294° C.

REFERENCE EXAMPLE 23

1-Cyclopropyl-8-(3,4-dimethyl-1-piperazinyl)-7-fluoro-4-oxo-1,4-dihydro-benzo[b][1,8]naphthyridine-3-carboxylic acid is prepared under the conditions of Reference Example 21 but starting from 1.9 g of 1-cyclopropyl-7-fluoro-8-(3-methyl-1-piperazinyl)-4-oxo-1,4-dihydro-benzo[b][1,8]naphthyridine-3-carboxylic acid, 1.38 cm³ of formic acid and 3.30 cm³ of a 30% aqueous solution of formaldehyde. After recrystallizing crude product from 50 cm³ of ethanol, 1.3 g of 1the cyclopropyl-8-(3,4-dimethyl-1-piperazinyl)-7-fluoro-4-oxo-1,4-dihydro-benzo[b][1,8]naphthyridine-3-carboxylic acid are obtained in the form of a yellow solid melting at 219° C.

REFERENCE EXAMPLE 24

A suspension of 0.47 g of 1-cyclopropyl-7,8-difluoro-4-oxo-1,4-dihydro-benzo[b][1,8]naphthyridine-3-carboxylic acid and 0.6 g of 1-methylpiperazine in 7 cm³ of dimethyl sulphoxide is heated at a temperature close to 80° C. for 15 minutes. The reaction mixture is poured into 25 cm³ of water and 9 cm³ of N hydrochloric acid are added. The solid obtained is drained and washed with 3 times 5 cm³ of water. After recrystallizing once from a mixture of 4.5 cm³ of ethanol and 4.5 cm³ of dimethylformamide, 0.29 g of 1-cyclopropyl-7-fluoro-8-(4-methyl-1-piperazinyl)-4-oxo-1,4-dihydro-benzo[b][1,8]naphthyridine-3-carboxylic acid is obtained in the form of a yellow solid melting at 250° C.

REFERENCE EXAMPLE 25

A suspension of 2 g of 7,8-difluoro-1-methoxy-4-oxo-1,4-dihydro-benzo[b][1,8]naphthyridine-3-carboxylic acid in 2.8 g of piperazine and 40 cm³ of dimethyl sulphoxide is stirred for 15 minutes at a temperature close to 40° C. After cooling to about 20° C., the reaction mixture is poured into 150 cm³ of water and 27.75 cm³ of 2N methanesulphonic acid are added. A very small amount of insoluble matter is removed by filtration through diatomaceous silica. 15 cm³ of 2N aqueous potassium hydroxide solution are added to the solution obtained. The precipitate formed is drained, washed with 3 times 15 cm³ of water and taken up in 100 cm³ of dimethylformamide and the mixture is heated, with stirring, for 10 minutes at a temperature close to 150° C. The suspension is cooled to about 100° C.; the insoluble matter is drained and taken up in 100 cm³ of ethanol and the mixture is heated at a temperature close to 75° C. for 1 hour. The insoluble matter is drained at about 50° C. and washed with 40 cm³ of the same solvent at the same temperature as above. 1.8 g of 7-fluoro-1-methoxy-4-oxo-8-(1-piperazinyl)-1,4-dihydro-benzo[b][1,8]naphthyridine-3-carboxylic acid are obtained in the form of a brown solid melting at 298°–300° C., solvated by 2.4% of water.

REFERENCE EXAMPLE 26

A suspension of 0.93 g of 7,8-difluoro-1-methoxy-4-oxo-1,4-dihydro-benzo[b][1,8]naphthyridine-3-carboxylic acid in 0.6 g of 1-methylpiperazine and 20 cm³ of dimethyl sulphoxide is heated at a temperature close to 80° C. for 5 minutes. After cooling to about 20° C., the reaction mixture is poured into 30 cm³ of water, 1.5 cm³ of 2N methanesulphonic acid are added and the product is drained and washed with 3 times 5 cm³ of water. After recrystallizing from 30 cm³ of dimethylformamide containing 30% of ethanol, 0.55 g of 7-fluoro-1-methoxy-8-(4-methyl-1-piperazinyl)-4-oxo-1,4-dihydro-benzo[b][1,8]naphthyridine-3-carboxylic acid is obtained in the form of a brown solid melting at 270° C.

REFERENCE EXAMPLE 27

A suspension of 2 g of 8-chloro-7-fluoro-1-methyl-4-oxo-1,4-dihydro-benzo[b][1,8]naphthyridine-3-carboxylic acid in 7.44 g of 2,2-dimethylpiperazine and 20 cm³ of pyridine is heated at a temperature close to 115° C. for 44 hours. Carrying out the reaction as described above in Reference Example 1, 1.6 g of 8-(3,3-dimethyl-1-piperazinyl)-7-fluoro-4-oxo-1,4-dihydro-benzo[b][1,8-]naphthyridine-3-carboxylic acid are obtained in the form of a yellow solid, solvated by 4.9% of water, melting at 362°–365° C.

REFERENCE EXAMPLE 28

A suspension of 4 g of 7,8,9-trifluoro-1-methyl-4-oxo-1,4-dihydro-benzo[b][1,8]naphthyridine-3-carboxylic acid in 60 cm³ of dimethyl sulphoxide and 3 g of 1-methylpiperazine is heated at 80° C. for 1 hour and a half. After cooling to about 20° C., 150 cm³ of water are added. 18 cm³ of 10% acetic acid are added to the solution obtained. The precipitate formed is drained, washed with 3 times 50 cm³ of water and recrystallized from 50 cm³ of dimethylformamide. 4 g of 7,9-difluoro-1-methyl-8-(4-methyl-1-piperazinyl)-4-oxo-1,4-dihydro-benzo[b][1,8]naphthyridine-3-carboxylic acid are obtained in the form of a yellow solid melting at 316° C.

REFERENCE EXAMPLE 29

A suspension of 2 g of 6,7,8-trifluoro-1-methoxy-4-oxo-1,4-dihydro-benzo[b][1,8]naphthyridine-3-carboxylic acid and 2.8 g of piperazine in 40 cm³ of dimethyl sulphoxide is heated, with stirring, at about 50° C. for 45 minutes. After cooling to a temperature close to 20° C., the suspension obtained is poured into 100 cm³ of water to which 9.22 g of methanesulphonic acid has been added. A small amount of insoluble matter is removed by filtration through diatomaceous silica. 32 cm³ of 2N aqueous potassium hydroxide solution are added to the filtrate. The precipitate obtained is drained, washed with 3 times 50 cm³ of water and recrystallized from 80 cm³ of dimethylformamide. 1.4 g of 7,9-difluoro-1-methoxy-4-oxo-8-(1-piperazinyl)-1,4-dihydro-benzo[b][1,8]naphthyridine-3-carboxylic acid are obtained in the form of a yellow solid melting at 305°–308° C.

REFERENCE EXAMPLE 30

A suspension of 1.2 g of 8-chloro-7-fluoro-1-(2-fluoroethyl)-4-oxo-1,4-dihydro-benzo[b][1,8]naphthyridine-3-carboxylic acid in 12 cm³ of pyridine and 3.52 g of 1-methylpiperazine is heated, with stirring, at a temperature close to 110° C. for 6 hours. After treatment under the conditions described in Reference Example 3, 0.6 g of 7-fluoro-1-(2-fluoroethyl)-8-(4-methyl-1-piperazinyl)-4-oxo-1,4-dihydro-benzo[b][1,8]naphthyridine-3-carboxylic acid is obtained in the form of a yellow solid melting at 306°–308° C.

The present invention also relates to pharmaceutical compositions intended for topical use which can be used in human and veterinary medicine and which contain, as active product, at least one product of general formula (I), in which R is other than a protective radical, in the pure form (in the free form or in the form of a salt) or in the form of a combination with one or more compatible and pharmaceutically acceptable diluents or adjuvants.

Solid compositions for topical application which can be used are powders, creams, pommades or gels. In these compositions the active product of general formula (I) is mixed with one or more inert diluents or adjuvants, such as lactose, cellulose derivatives or talc for example. These compositions can also contain other substances, such as, for example, fatty acids and their derivatives or fatty substances of animal, vegetable or synthetic origin.

Liquid compositions which can be used are emulsions which are pharmaceutically acceptable for topical application, solutions and suspensions containing inert diluents such as water, oils (paraffin oil, white petroleum jelly oil, olive oil . . . ) or organic esters . . . These compositions can also contain adjuvants such as wetting agents, emulsifiers, dispersants or stabilizers.

The compositions can also be prepared in the form of solid compositions which can be dissolved at the time of use.

The compositions containing a product of general formula (I) are particularly useful for the treatment of cutaneous infections by staphylococci.

In general, the compositions contain concentrations of from 0.1 °/$_{oo}$ to 1 °/$_{oo}$.

The following example illustrates a composition for topical application containing a product of general formula (I).

EXAMPLE

| EXAMPLE | |
|---|---|
| 1-cyclopropyl-7,8-difluoro-4-oxo-1,4-dihydro-benzo[b][1,8]naphthyridine-3-carboxylic acid | 1 g |
| zinc oxide | 1.5 g |
| talc q.s. | 100 g |

Finally, the products of general formula (I) can also be used as preservatives or disinfectants for organic or inorganic materials. In particular in the dyestuffs, fatty matter, paper, wood and polymer industries or in the textile industry, the foodstuffs industry or water treatment. It is also understood that the compositions intended for preservation or as disinfectants and containing a product of general formula (I) in the pure form or in the form of a combination with compatible diluents or adjuvants, also fall within the scope of the present invention.

We claim:

1. A new benzo[b][1,8]naphthyridine derivative, comprising a compound of the formula:

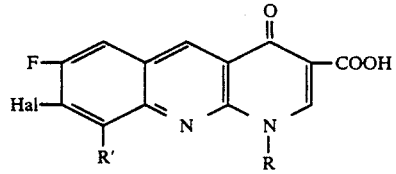

in which:

R represents a hydrogen atom, an alkyl or fluoroalkyl radical, a cycloalkyl radical containing 3 to 6 carbon atoms, or an alkoxy or alkyl radical or radical including trimethylsilyl, trityl, benzhydryl, tetrahydropyrannyl, formyl, acetyl, chloroacetyl, trichloroacetyl, trifluoroacetyl, methoxycarbonyl, ethoxycarbonyl, t.butoxycarbonyl, trichloroethoxycarbonyl, ethoxymethyl and methoxymethyl, and either Hal represents a fluorine, chlorine or bromine atom and R' represents a hydrogen atom, or the symbols Hal and R' simultaneously represent fluorine atoms, it being understood that the alkyl radicals cited above are straight-chain or branched and contain 1 to 4 carbon atoms, or a metal salt or addition salt with nitrogenous bases thereof.

2. A new benzo[b][1,8]naphthyridine derivative according to claim 1, wherein:

R represents a hydrogen atom, an alkyl radical containing 1 to 4 carbon atoms or a fluoroethyl, cyclopropyl, methoxy or methylamino radical and either Hal represents a fluorine or chlorine atom and R' represents a hydrogen atom, or Hal and R' simultaneously represent fluorine atoms, or a metal salt or an addition salt with nitrogenous bases thereof.

3. 7,8-Difluoro-1-methyl-4-oxo-1,4-dihydro-benzo[b][1,8]naphthyridine-3-carboxylic acid or a metal salt or an addition salt with nitrogenous bases thereof.

4. 8-Chloro-7-fluoro-1-methyl-4-oxo-1,4-dihydro-benzo[b][1,8]naphthyridine-3-carboxylic acid or a metal salt or an addition salt with nitrogenous bases thereof.

5. 1-Methyl-4-oxo-7,8,9-trifluoro-1,4-dihydro-benzo[b][1,8]naphthyridine-3-carboxylic acid or a metal salt or an addition salt with nitrogenous bases thereof.

6. 7,8-Difluoro-1-methoxy-4-oxo-1,4-dihydro-benzo[b][1,8]naphthyridine-3-carboxylic acid or a metal salt or an addition salt with nitrogenous bases thereof.

7. 1-Cyclopropyl-7,8-difluoro-4-oxo-1,4-dihydro-benzo[b][1,8]naphthyridine-3-carboxylic acid or a metal salt or an addition salt with nitrogenous bases thereof.

8. An antimicrobial composition comprising an effective amount of at least one derivative according to claim 1, in which R is defined as in claim 1 with the exception of representing a radical including trimethylsilyl, trityl, benzhydryl, tetrahydropyrannyl, formyl, acetyl, chloroacetyl, trichloroacetyl, trifluoroacetyl, methoxycarbonyl, ethoxycarbonyl, t.butoxycarbonyl, trichloroethoxycarbonyl, ethoxymethyl and methoxymethyl, in the pure form or in combination with one or more compatible diluents or adjuvants.

* * * * *